(12) United States Patent
Ichimura et al.

(10) Patent No.: US 9,802,040 B2
(45) Date of Patent: Oct. 31, 2017

(54) BODY MOTION DETECTION DEVICE AND HUMAN BODY STIMULATION APPARATUS COMPRISING SAID DEVICE

(71) Applicant: Panasonic Intellectual Property Management Co., Ltd., Osaka (JP)

(72) Inventors: Ryo Ichimura, Shiga (JP); Izumi Mihara, Osaka (JP); Keita Inui, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 126 days.

(21) Appl. No.: 14/425,511

(22) PCT Filed: Sep. 25, 2013

(86) PCT No.: PCT/JP2013/005680
§ 371 (c)(1),
(2) Date: Mar. 3, 2015

(87) PCT Pub. No.: WO2014/057619
PCT Pub. Date: Apr. 17, 2014

(65) Prior Publication Data
US 2015/0224308 A1    Aug. 13, 2015

(30) Foreign Application Priority Data
Oct. 11, 2012    (JP) ................................ 2012-226092

(51) Int. Cl.
*A61B 5/00*     (2006.01)
*A61N 1/36*     (2006.01)
(Continued)

(52) U.S. Cl.
CPC ........ *A61N 1/36003* (2013.01); *A61B 5/1123* (2013.01); *A61B 5/6828* (2013.01);
(Continued)

(58) Field of Classification Search
CPC ..................... A61B 5/11; A61B 5/112; A61B 5/1121–5/23; A61B 5/1126;
(Continued)

(56) References Cited

U.S. PATENT DOCUMENTS 8,626,472 B2 * 1/2014 Solinsky ................ A61B 5/112
                                                235/105
9,149,213 B2 * 10/2015 Niemimaki ............ A61B 5/112
(Continued)

FOREIGN PATENT DOCUMENTS

JP    2002-355236 A    12/2002
JP    2004-167056 A     6/2004
(Continued)

OTHER PUBLICATIONS

Chinese Office Action issued in Chinese Application No. 201380046227.3 dated Sep. 25, 2015.
(Continued)

*Primary Examiner* — Max Hindenburg
(74) *Attorney, Agent, or Firm* — McDermott Will & Emery LLP

(57) ABSTRACT

The human body stimulation apparatus comprises a left detection unit, a right detection unit, a determination unit, a control unit, a right stimulation unit and a left stimulation unit. The detection units generate a detection signal according to a walking motion of a human body. The determination unit divides the walking motion of one walking cycle into multiple walking stages on the basis of the detection signal. The determination unit determines that the walking motion is stopped on the basis of at least one duration time of the walking stages. The control unit controls the magnitude of the stimulation that the right stimulation unit and the left stimulation unit apply to the human body on the basis of the determination results of the determination unit.

11 Claims, 15 Drawing Sheets

(51) Int. Cl.
*A61B 5/11* (2006.01)
*A61N 1/04* (2006.01)

(52) U.S. Cl.
CPC ......... *A61N 1/0452* (2013.01); *A61N 1/0476* (2013.01); *A61N 1/36014* (2013.01); *A61N 1/0484* (2013.01)

(58) Field of Classification Search
CPC . A61B 5/1127; A61B 5/6828; A61N 1/36003; A61N 1/0452; A61N 1/0476; A61N 1/0484
See application file for complete search history.

(56) References Cited

U.S. PATENT DOCUMENTS

| | | | |
|---|---|---|---|
| 9,216,131 B2* | 12/2015 | Nakashima | A61H 3/00 |
| 9,357,948 B2* | 6/2016 | Youssef | A61B 5/11 |
| 9,591,993 B2* | 3/2017 | Morris Bamberg | A61B 5/1038 |

| | | |
|---|---|---|
| 2012/0226203 A1 | 9/2012 | Nakashima et al. |

FOREIGN PATENT DOCUMENTS

| | | |
|---|---|---|
| JP | 2004-329520 A | 11/2004 |
| JP | 2005-205001 A | 8/2005 |
| JP | 2009-106537 A | 5/2009 |
| JP | 2012-000343 A | 1/2012 |
| JP | 2012-065723 A | 4/2012 |
| JP | 2013-123532 A | 6/2013 |
| WO | 2011-058641 A1 | 5/2011 |

OTHER PUBLICATIONS

Japanese Office Action issued in Japanese Application No. 2012-226092 dated Mar. 1, 2016, with English Translation.
International Preliminary Report on Patentability issued in International Application No. PCT/JP2013/005680 dated Apr. 14, 2015.
International Search Report issued in PCT/JP2013/005680, dated Oct. 29, 2013, with English translation.

* cited by examiner

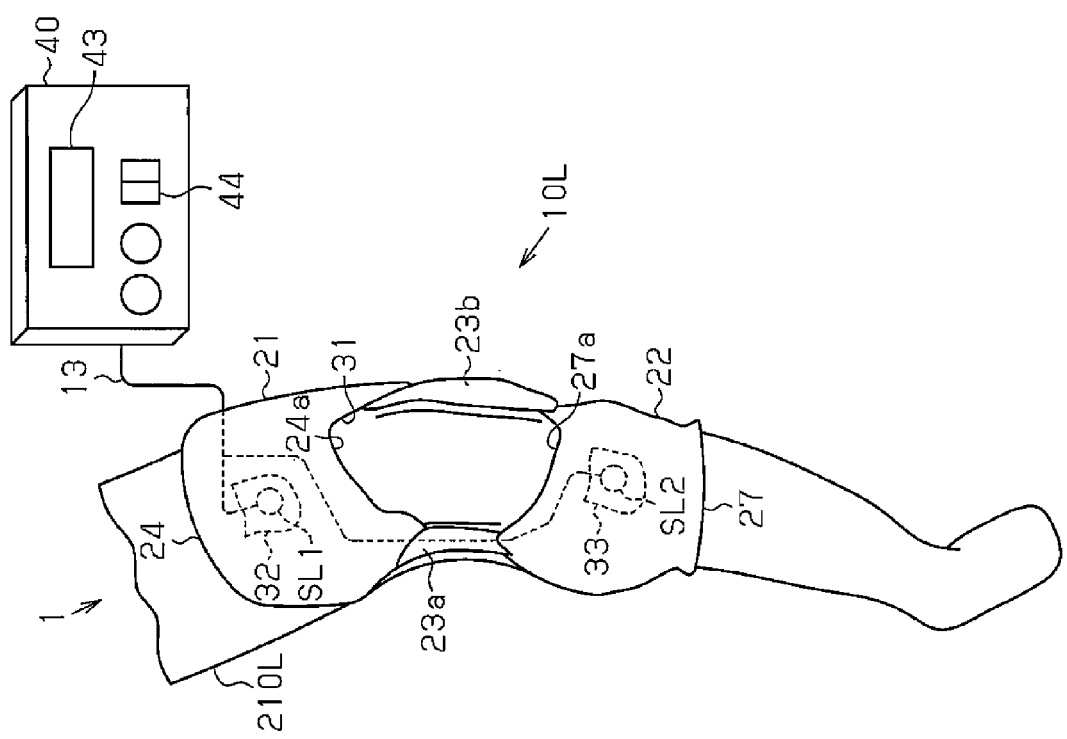

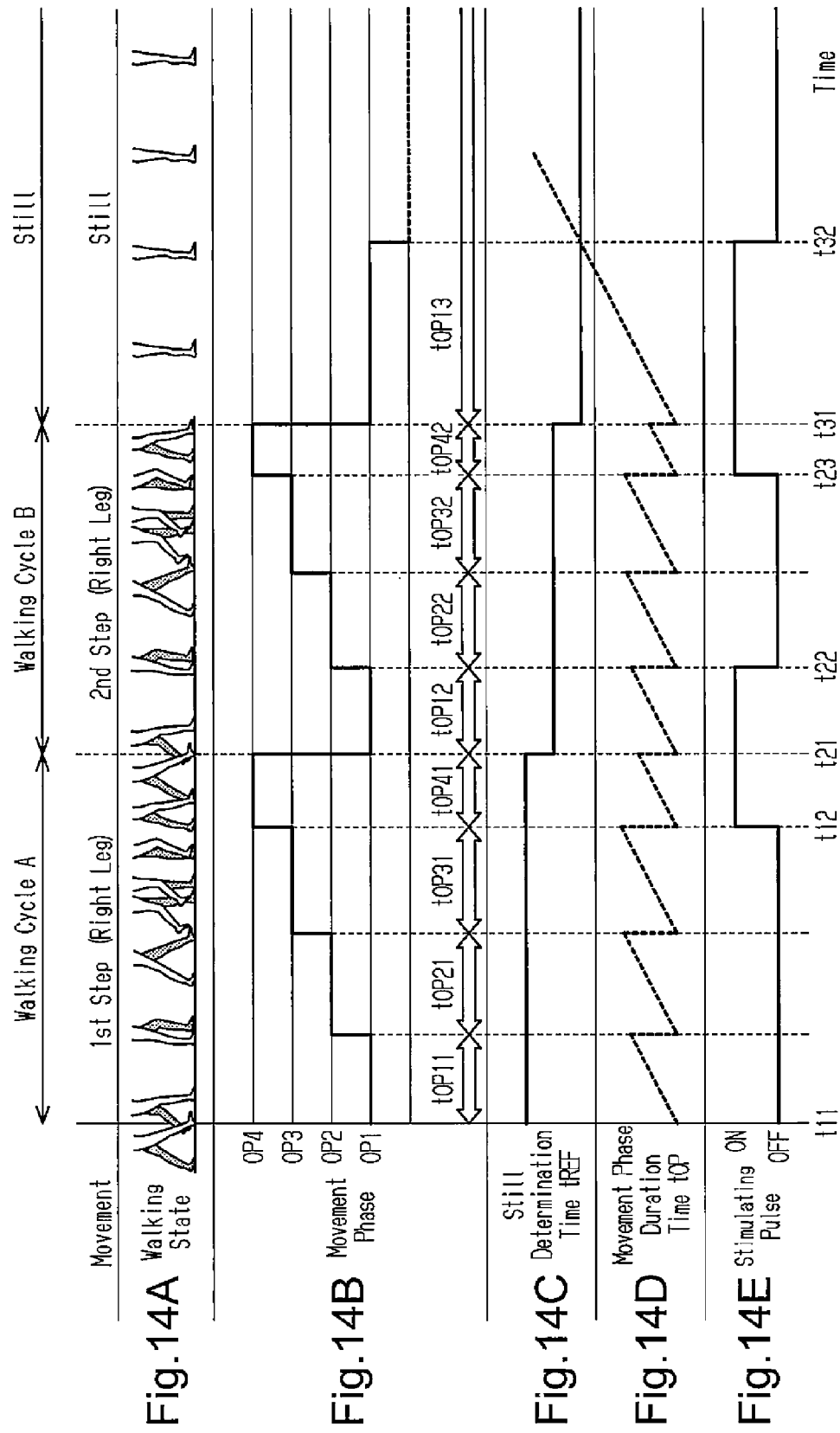

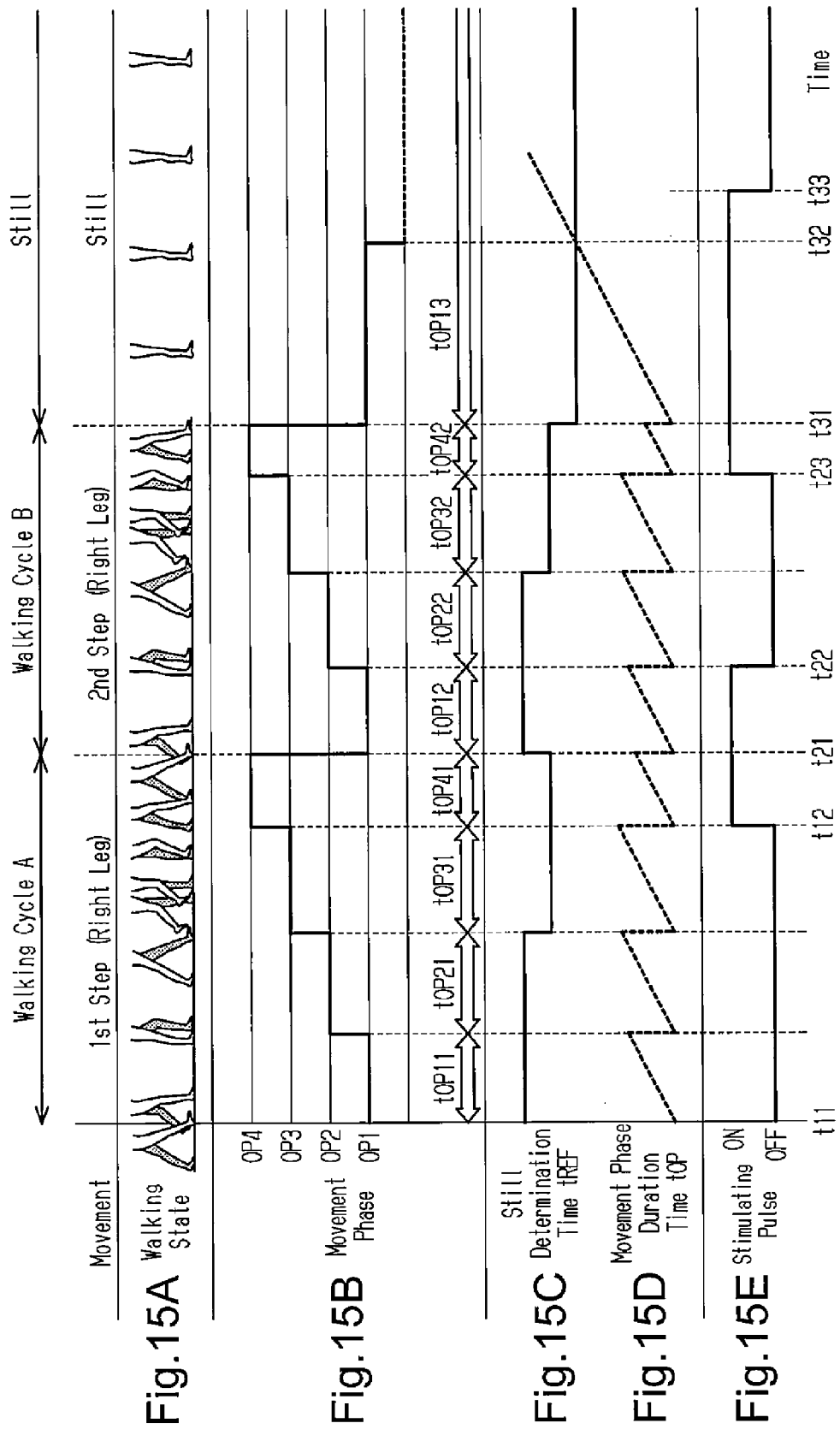

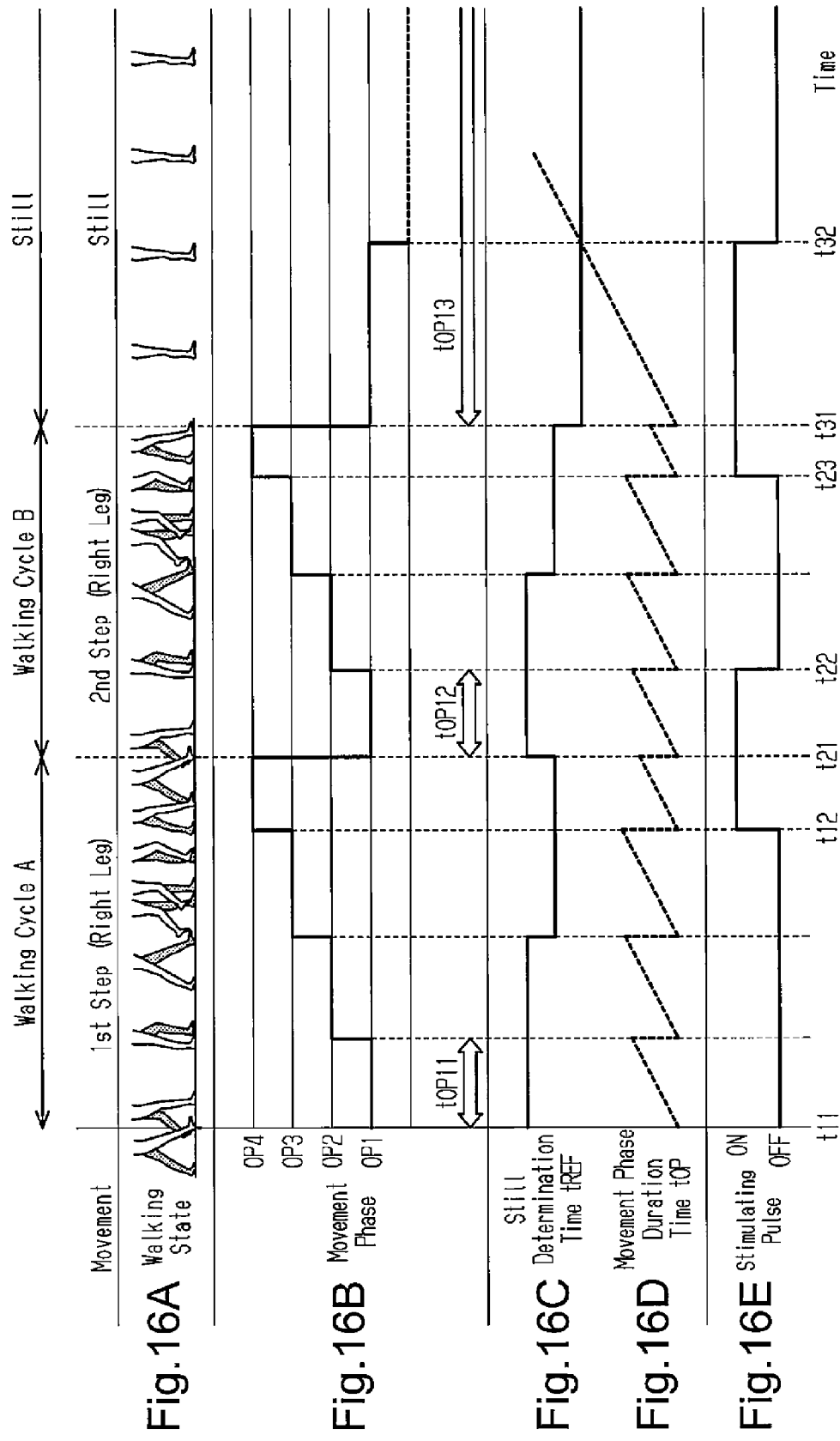

BODY MOTION DETECTION DEVICE AND HUMAN BODY STIMULATION APPARATUS COMPRISING SAID DEVICE

RELATED APPLICATIONS

This application is the U.S. National Phase under 35 U.S.C. §371 of International Application No. PCT/JP2013/005680, filed on Sep. 25, 2013, which in turn claims the benefit of Japanese Application No. 2012-226092, filed on Oct. 11, 2012, the disclosures of which Applications are incorporated by reference herein.

TECHNICAL FIELD

The present invention relates to a body motion detection device that detects a body motion, and a human body stimulus applying device that applies stimulus to the human body.

BACKGROUND ART

The human body stimulus applying device using the body motion detection device of the prior art includes an acceleration sensor, an electrical stimulus applying portion, and a control unit. The acceleration sensor is attached to the femoral region. The control unit predicts a timing the foot of the user moves away from the floor based on an output signal of the acceleration sensor. The control unit provides a signal for flowing current from the electrical stimulus applying portion to the thigh at the predicted timing. The electrical stimulus applying portion applies the electrical stimulus to the thigh in accordance with the signal provided from the control unit. Patent document 1 discloses an example of the conventional human body stimulus applying device.

PRIOR ART DOCUMENT

Patent Document

Patent Document 1: Japanese Laid-Open Patent Publication No. 2002-355236

SUMMARY OF THE INVENTION

Problems that are to be Solved by the Invention

When an electrical stimulus is applied to a leg, for example, while a walking movement of the human body is still, a great load may be imposed on the leg. The control unit of the conventional human body stimulus applying device predicts the timing the foot moves away from the floor on the premise of a periodic walking movement. Thus, if the actual walking movement differs from the periodic walking movement, the predicted timing greatly differs from the actual movement of the foot. The electrical stimulus thus may be applied on the leg while the walking movement is still.

The present invention has been conceived on the basis of the above background and it is an object to provide a body motion detection device that can appropriately determine whether or not the walking movement is still, and a human body stimulus applying device including such a device.

Means for Solving the Problems (1) One aspect of the present invention provides a body motion detection device that detects movement of a human body. The body motion detection device includes a detection unit that generates a detection signal that changes according to a walking movement of the human body. An evaluation unit separates the walking movement of one walking cycle into a plurality of walking phases based on the detection signal generated by the detection unit. The evaluation unit determines whether or not the walking movement is still based on a duration time of at least one of the walking phases.

(2) Preferably, the one walking cycle includes a stance phase and a swing phase that defined as specific walking phases. The evaluation unit separates the stance phase or the swing phase into a plurality of walking phases, defines each of the separated walking phases as a divided walking phase, and determines whether or not the walking movement is still based on a duration time of each of the divided walking phases.

(3) Preferably, the evaluation unit determines that the walking movement is still when the duration time of at least one of the divided walking phases is longer than a still determination time.

(4) Preferably, the evaluation unit includes a measurement unit that measures the duration time of each of the divided walking phases. The evaluation unit determines whether or not the walking movement is still based on a comparison of the duration time of at least one of the divided walking phases measured by the measurement unit with the still determination time.

(5) Preferably, the body motion detection device further includes a time setting unit that sets the still determination time based on the duration time of at least one of the walking phases measured by the measurement unit.

(6) Preferably, the time setting unit sets the still determination time based on at least one of the duration times measured by the measurement unit before a current walking cycle.

(7) Preferably, the time setting unit includes a determination time defining unit that sets a relationship of the duration time of each of the divided walking phases and the still determination time. The determination time defining unit outputs the still determination time based on the relationship when the duration time of the divided walking phase is received from the measurement unit.

(8) Preferably, the detection unit includes a right body detector and a left body detector. The right body detector includes a first right body sensor that generates an output signal corresponding to a movement of a first right body region and a second right body sensor that generates an output signal corresponding to a movement of a second right body region. The left body detector includes a first left body sensor that generates an output signal corresponding to a movement of a first left body region and a second left body sensor that generates an output signal corresponding to a movement of a second left body region. The evaluation unit determines whether or not the walking movement is still based on at least one of the output signal of the first right body sensor, the output signal of the first left body sensor, the output signal of the second right body sensor, and the output signal of the second left body sensor.

(9) A further aspect of the present invention is a human body stimulus applying device that applies stimulus to a human body, the human body stimulus applying device includes the body motion detection device, a control unit that transmits a command signal to a stimulus applying portion based on a determination result of the body motion detection device, and a stimulus applying portion that changes a magnitude of the stimulus to apply to the human body based on the command signal.

(10) Preferably, the stimulus applying portion includes a right body stimulus applying portion that applies stimulus to a right body, and a left body stimulus applying portion that applies stimulus to a left body. The evaluation unit includes a first evaluation unit and a second evaluation unit. The first evaluation unit determines whether or not the walking movement is still based on the output signal of the first right body sensor and the output signal of the second right body sensor. The second evaluation unit determines whether or not the walking movement is still based on the output signal of the first left body sensor and the output signal of the second left body sensor. The control unit transmits a command signal to the right body stimulus applying portion and applies stimulus to the human body when the first evaluation unit determines that the walking movement is still, and the control unit transmits a command signal to the left body stimulus applying portion to have stimulus applied to the human body when the second evaluation unit determines that the walking movement is still.

(11) Preferably, the control unit transmits the command signal to the stimulus applying portion after a walking still time, which is an elapsed time from when determined that the walking movement is still, exceeds a determination elapsed time.

(12) Preferably, the stimulus applying portion applies an electrical stimulus to the human body.

Effect of the Invention

The body motion detection device and human body stimulus applying device can appropriately determine whether or not the walking movement is still.

BRIEF DESCRIPTION OF THE DRAWINGS

FIG. 1 is a schematic view of a human body stimulus applying device according to a first embodiment of the present invention.

FIG. 2 is a front view of a human body attached with an attachment unit according to the first embodiment of the present invention.

FIG. 6A shows the walking cycle, FIG. 6B shows the walking movement, FIG. 6C shows a combination signal Z1, and FIGS. 6D, 6E, and 6F show the movement phase.

FIGS. 14A to 14E are graphs showing one example of a change in parameters associated with the operation of the human body stimulus applying device of the third embodiment of the present invention, where FIG. 14A shows a walking state, FIG. 14B shows a movement phase, FIG. 14C shows a still determination time, FIG. 14D shows a movement phase duration time, and FIG. 14E shows a relationship of a stimulating pulse waveform and time.

FIGS. 15A to 15E are graphs showing one example of a change in parameters associated with the operation of the human body stimulus applying device of a fourth embodiment of the present invention, where FIG. 15A shows a walking state, FIG. 15B shows a movement phase, FIG. 15C shows a still determination time, FIG. 15D shows a movement phase duration time, and FIG. 15E shows a relationship of a stimulating pulse waveform and time.

FIGS. 16A to 16E are graphs showing one example of a change in parameters associated with the operation of the human body stimulus applying device of other embodiments of the present invention, where FIG. 16A shows a walking state, FIG. 16B shows a movement phase, FIG. 16C shows a still determination time, FIG. 16D shows a movement phase duration time, and FIG. 16E shows a relationship of a stimulating pulse waveform and time.

EMBODIMENTS OF THE INVENTION

First Embodiment

Figure 3:
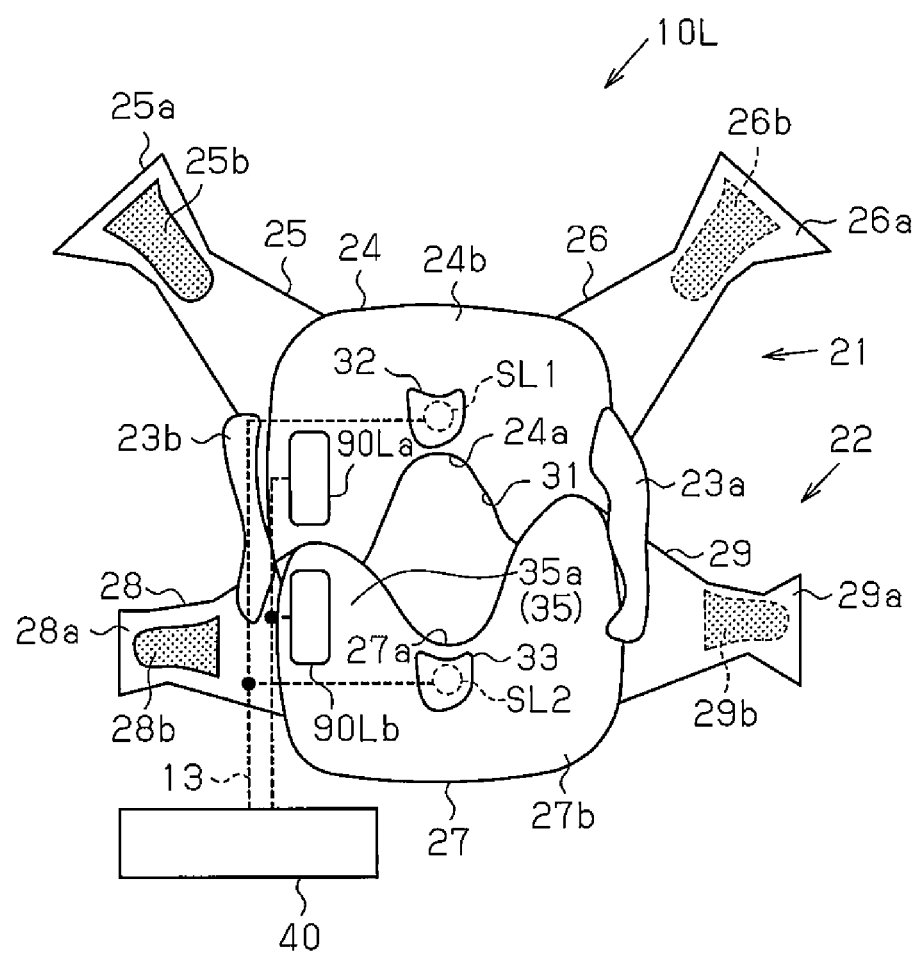
FIG. 3 is a rear view of the attachment unit according to the first embodiment of the present invention.

A schematic configuration of a human body stimulus applying device 1 using a body motion detection device will now be described with reference to FIG. 1.

The human body stimulus applying device 1 includes a stimulation device main body unit 40 and a first attachment unit 10L. The first attachment unit 10L is attached to a left leg 210L of a user 200 (see FIG. 2). The human body stimulus applying device 1 includes the first attachment unit 10L and a second attachment unit 10R to be attached to a left leg 210L and a right leg 210R of the user 200, respectively. The right leg 210R and the second attachment unit 10R have the same structure as the left leg 210L and the first attachment unit 10L, respectively, and thus the illustration and the description of the right leg 210R and the second attachment unit 10R will be omitted. The first attachment unit 10L and the second attachment unit 10R detect the movement of the user 200 in a walking movement of the user 200. The stimulation device main body unit 40 divides the movement in one walking cycle of the user 200 to a plurality of movement phases to determine the movement of each movement phase based on the detection results of the first attachment unit 10L and the second attachment unit 10R.

The stimulation device main body unit 40 applies stimulus with respect to the user 200 based on the movement determination result in the movement phase divided into plurals. The stimulation device main body unit 40 carries out a control of determining a walking still state of the user 200 (i.e., determining that the walking movement is still), and stopping the application of the stimulus.

The stimulation device main body unit 40 includes a display unit 43 and an operation unit 44. A connection cable 13 connects the stimulation device main body unit 40 and the first attachment unit 10L to each other, and connects the stimulation device main body unit 40 and the second attachment unit 10R to each other. The first attachment unit 10L includes a first left body sensor SL1 and a second left body sensor SL2. Each of the first left body sensor SL1 and the second left body sensor SL2 detects a displacement of a physical quantity of a femoral region and a knee region of the user 200.

As shown in FIG. 2, when the user 200 attaches the first attachment unit 10L and the second attachment unit 10R, the first left body sensor SL1 and the second left body sensor SL2 are attached to the left leg, which is a first region, of the user 200, and a first right-side sensor SR1 and a second right-side sensor SR2 are attached to the right leg, which is a second region, of the user 200.

A configuration of the first attachment unit 10L will now be described with reference to FIG. 3.

The first attachment unit 10L includes an upper thigh attachment section 21 to be attached to the femoral region of the left leg 210L and a lower thigh attachment section 22 to be attached to a leg region. The upper thigh attachment section 21 and the lower thigh attachment section 22 are coupled to each other by a first coupling portion 23a and a second coupling portion 23b.

The upper thigh attachment section 21 includes an upper thigh front portion 24, a first upper thigh rear portion 25, and a second upper thigh rear portion 26. The upper thigh front portion 24 covers a front portion and a part of a side surface of the femoral region of the left leg 210L. The first upper thigh rear portion 25 and the second upper thigh rear portion 26 are respectively formed at first and second ends of the upper thigh front portion 24. The upper thigh front portion 24 has a recess 24a formed at a lower end portion. The first upper thigh rear portion 25 includes a first connecting portion 25b at a first distal end portion 25a. The second upper thigh rear portion 26 includes a second connecting portion 26b at a second distal end portion 26a. The first connecting portion 25b and the second connecting portion 26b are connected to each other in a freely detachable manner. The first connecting portion 25b and the second connecting portion 26b are connected to each other at a rear portion of the femoral region of the left leg 210L, so that the upper thigh attachment section 21 is attached to the femoral region of the left leg 210L. The upper thigh attachment section 21 includes a left body stimulus applying unit 90La. The left body stimulus applying unit 90La applies stimulus to the femoral region of the user 200 according to the control from the stimulation device main body unit 40.

The lower thigh attachment section 22 includes a lower thigh front portion 27, a first lower thigh rear portion 28, and a second lower thigh rear portion 29. The lower thigh front portion 27 covers a front portion and a part of the side surface of the leg region of the left leg 210L. The first lower thigh rear portion 28 and the second lower thigh rear portion 29 are respectively formed at first and second ends of the lower thigh front portion 27. The lower thigh front portion 27 has a recess 27a formed at an upper end portion. The first lower thigh rear portion 28 includes a third connecting portion 28b at a third distal end portion 28a. The second lower thigh rear portion 29 includes a fourth connecting portion 29b at a fourth distal end portion 29a. The third connecting portion 28b and the fourth connecting portion 29b are connected to each other in a freely detachable manner. The third connecting portion 28b and the fourth connecting portion 29b are connected to each other at a rear portion of the leg region of the left leg 210L, so that the lower thigh attachment section 22 is attached to the leg region of the left leg 210L. The lower thigh attachment section 22 includes a left body stimulus applying unit 90Lb. The left body stimulus applying unit 90Lb applies stimulus to the leg region of the user 200 according to the control from the stimulation device main body unit 40.

The first coupling portion 23a and the second coupling portion 23b are made from a stretchable member, for example. The first coupling portion 23a couples the first end of the upper thigh attachment section 21 to the first end of the lower thigh attachment section 22, and the second coupling portion 23b couples the second end of the upper thigh attachment section 21 to the second end of the lower thigh attachment section 22. When the upper thigh attachment section 21 and the lower thigh attachment section 22 are coupled to each other, an attachment hole 31 surrounded by the recess 24a of the upper thigh front portion 24, the recess 27a of the lower thigh front portion 27, the first coupling portion 23a, and the second coupling portion 23b is formed in the first attachment unit 10L. At the time of attaching the first attachment unit 10L, the front portion of the knee of the left leg 210L is exposed from the attachment hole 31 thus facilitating the bending movement of the knee joint in the walking movement.

The upper thigh front portion 24 and the lower thigh front portion 27 respectively includes a first inserting part 32 and a second inserting part 33 at substantially a central portion. The first left body sensor SL1 and the second left body sensor SL2 are arranged in the first inserting part 32 and the second inserting part 33, respectively. In the second attachment unit 10R, the first right body sensor SR1 and the second right body sensor SR2 are respectively arranged at positions symmetrical with the first left body sensor SL1 and the second left body sensor SL2. The first left body sensor SL1 and the first right body sensor SR1 respectively arranged at the upper thigh front portion 24 of the first attachment unit 10L and the second attachment unit 10R are, for example, angular speed sensors. The second left body sensor SL2 and the second right body sensor SR2 respectively arranged at the lower thigh front portion 27 of the first attachment unit 10L and the second attachment unit 10R are, for example, angular speed sensors. If the first left body sensor SL1 and the first right body sensor SR1 are angular speed sensors, the first left body sensor SL1 and the first right body sensor SR1 output an acceleration of the femoral region that turns with the hip joint of the left leg 210L and the right leg 210R as a center in the walking movement. If the second left body sensor SL2 and the second right body sensor SR2 are angular speed sensors, the second left body sensor SL2 and the second right body sensor SR2 output an acceleration of the leg region that turns with the knee joint of the left leg 210L and the right leg 210R as a center.

The first attachment unit 10L detects the displacement of the knee joint in the walking state using the first left body sensor SL1 and the second left body sensor SL2. The second attachment unit 10R detects the displacement of the knee joint in the walking state using the first right body sensor SR1 and the second right body sensor SR2.

As shown in FIG. 2, the first left body sensor SL1 attached to the upper part of the left lower crotch of the user 200 and the first right body sensor SR1 attached to the upper part of the right lower crotch are arranged at symmetrical positions to each other with respect to a reference plane 200C. The reference plane 200C is a plane that becomes the center of the symmetrical movement of the user 200. Specifically describing, the reference plane 200C includes a median plane, which is a plane of the center of the body that divides the body of the user 200 seen from the walking direction (body of the user 200 seen from the front) evenly to the left and right. Furthermore, the second left body sensor SL2 attached to a lower part of the left lower crotch of the user 200 and the second right body sensor SR2 attached to the lower part of the right lower crotch are arranged at symmetrical positions to each other with respect to the reference plane 200C.

The first left body sensor SL1 and the second left body sensor SL2 attached to the left lower crotch of the user 200 configure a left leg detection unit SL that detects the movement of the left leg of the user 200. The first right body sensor SR1 and the second right body sensor SR2 attached to the right lower crotch configure a right leg detection unit SR that detects the movement of the right leg of the user.

The walking movement of the user 200 will now be described with reference to FIG. 4.

When performing the walking movement, the user 200 carries out the movement of the legs shown in FIG. 4A. The portion indicated with only a solid line in FIG. 4A indicates the movement of the right leg of the user 200. The portion indicated with hatching in FIG. 4A indicates the movement of the left leg of the user 200. When the user 200 performs the walking movement with the movements of the legs shown in FIG. 4A, the period in the walking movement is defined as shown in FIGS. 4B to 4E. One walking cycle of the user 200 is a period from when the heel of one foot touches the ground until the same heel again touches the ground. In the one walking cycle, a zone in which the foot of the user is touching the floor is a stance phase, and a zone in which the foot is not touching the floor is a swing phase. In the walking movement, the right leg and the left leg alternately repeat the stance phase and the swing phase. If one leg changes from the swing phase to the stance phase, the other leg changes from the stance phase to the swing phase with a temporal shift. Thus, the one walking cycle includes a zone in which both feet are touching the ground.

Figure 4:
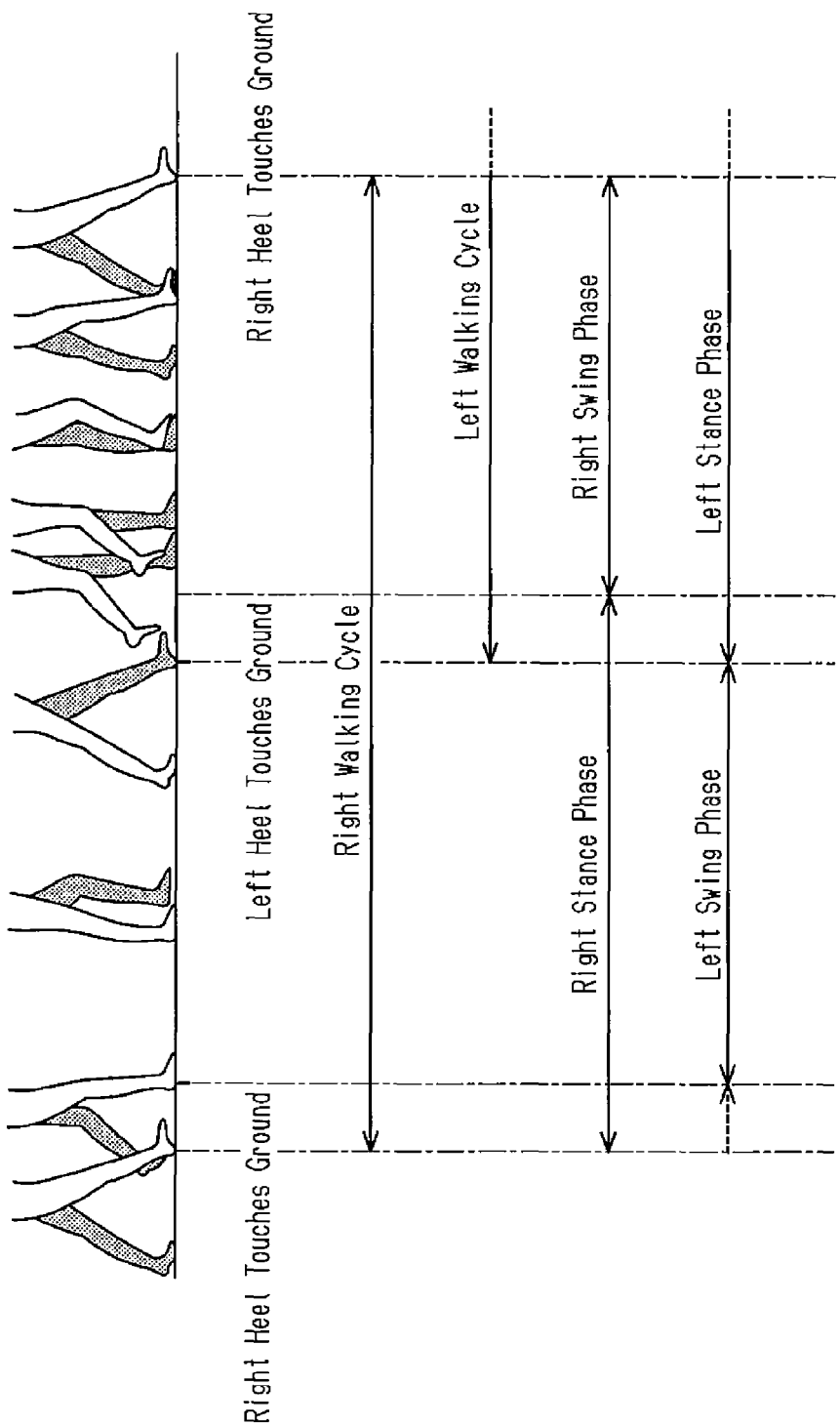
FIG. 4A is a view showing the movement of both legs in a walking movement of the human body.
FIGS. 4B and 4C are views showing one walking cycle.
FIG. 4D is a view showing a period of the movement of the right leg.
FIG. 4E is a view showing a period of the movement of the left leg.

The human body stimulus applying device 1 determines the stance phase and the swing phase in one walking cycle shown in FIG. 4. The human body stimulus applying device 1 defines the stance phase and the swing phase as specific walking phases. The human body stimulus applying device 1 separates the stance phase and the swing phase defined as the specific walking phases into a plurality of phases. The human body stimulus applying device 1 defines each of the plurality of phases as a divided walking phase, and carries out movement determination including the still state. The human body stimulus applying device 1 controls the stimulus applying portion based on the movement determination result of the divided walking phase divided into plurals.

Figure 5:
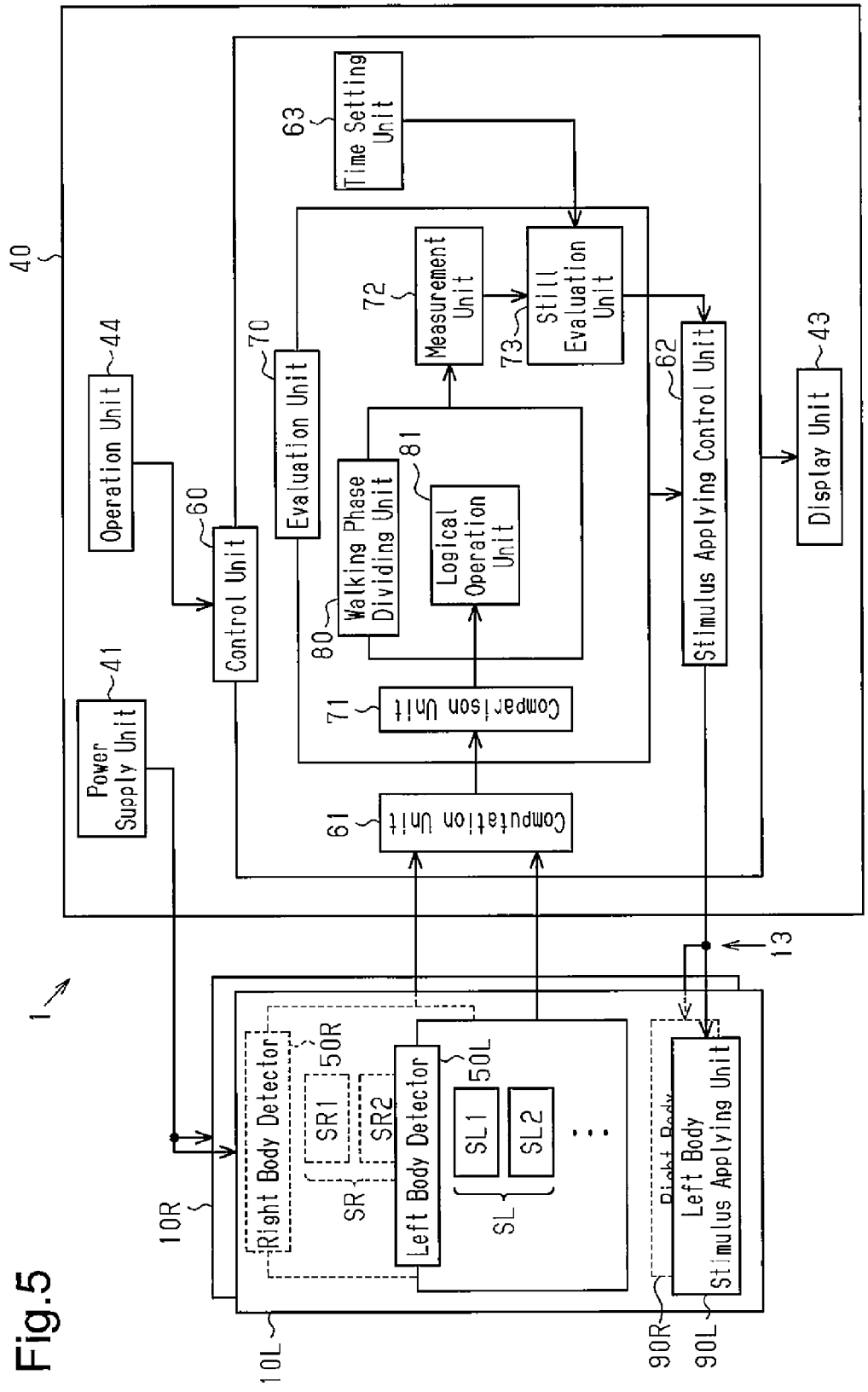
FIG. 5 is a circuit block diagram of the human body stimulus applying device according to the first embodiment of the present invention.

A circuit block configuration of the human body stimulus applying device 1 will now be described with reference to FIG. 5.

The human body stimulus applying device 1 includes the first attachment unit 10L, the second attachment unit 10R, and the stimulation device main body unit 40. The first attachment unit 10L includes a left body detector 50L and a left body stimulus applying unit 90L. The left body detector 50L includes the left leg detection unit SL. The second attachment unit 10R includes a right body detector 50R and a right body stimulus applying unit 90R. The right body detector 50R includes a right leg detection unit SR. The stimulation device main body unit 40 includes a power supply unit 41, the display unit 43, the operation unit 44 and a control unit 60. The control unit 60 includes an computation unit 61, a stimulus applying control unit 62, a time setting unit 63, and an evaluation unit 70. The evaluation unit 70 includes a comparison unit 71, a measurement unit 72, a still evaluation unit 73, and a walking phase dividing unit 80. The walking phase dividing unit 80 includes a logical operation unit 81. Each of the output of the power supply unit 41 and the output signal of the stimulus applying control unit 62 of the stimulation device main body unit 40 are provided to the first attachment unit 10L and the second attachment unit 10R through the connection cable 13. Each of the detection signal from the left leg detection unit SL of the first attachment unit 10L and the detection signal from the right leg detection unit SR of the second attachment unit 10R are provided to the stimulation device main body unit 40 through the connection cable 13.

The operation of each circuit block in the human body stimulus applying device 1 will be hereinafter described.

The first left body sensor SL1 and the second left body sensor SL2 included in the left leg detection unit SL detect the movement of the left leg 210L of the user 200 attached with the first attachment unit 10L, and generate a detection signal. The first right body sensor SR1 and the second right body sensor SR2 included in the right leg detection unit SR detect the movement of the right leg 210R of the user 200 attached with the second attachment unit 10R, and generate a detection signal.

The detection signal from the first left body sensor SL1 of the left leg detection unit SL is a first detection signal IL1, and is transmitted to the computation unit 61. The detection signal from the second left body sensor SL2 of the left leg detection unit SL is a second detection signal IL2, and is transmitted to the computation unit 61. The detection signal from the first right body sensor SR1 of the right leg detection unit SR is a third detection signal IR1, and is transmitted to the computation unit 61. The detection signal from the second right body sensor SR2 of the right leg detection unit SR is a fourth detection signal IR2, and is transmitted to the computation unit 61.

The computation unit 61 receives the first detection signal IL1, the second detection signal IL2, the third detection signal IR1, and the fourth detection signal IR2, and carries out signal processing on the signals. The computation unit 61 carries out removal of noise such as high frequency component, and the like, calculation of movement average value, frequency analysis, and the like, for example, for the signal processing. The computation unit 61 carries out a process of combining the first detection signal IL1 and the third detection signal IR1 of the first left body sensor SL1 and the first right body sensor SR1 symmetrically arranged with respect to the reference plane 200C. The computation unit 61 carries out a process of combining the second detection signal IL2 and the fourth detection signal IR2 of the second left body sensor SL2 and the second right body sensor SR2 symmetrically arranged with respect to the reference plane 200C. The computation unit 61 carries out a subtraction process (IL1−IR1) and an addition process (IL1+IR1) of the first detection signal IL1 and the third detection signal IR1, for example, for the combining process. The computation unit 61 carries out a subtraction process (IL2−IR2) and an addition process (IL2+IR2) of the second detection signal IL2 and the fourth detection signal IR2, for example, for the combining process. The computation unit 61 combines the first detection signal IL1, the second detection signal IL2, the third detection signal IR1, and the fourth detection signal IR2, for example, according to the following equation (1) to generate a combination signal Z1.

$$Z1=aX1+bX2+cX3+dX4+\ldots+C \quad (1)$$

Where, a, b, c, and d in equation (1) are coefficients. C in equation (1) is a constant. The values of the first detection signal IL1, the second detection signal IL2, the third detection signal IR1, and the fourth detection signal IR2, for example, are substituted to variables X1, X2, X3, and X4. Furthermore, for example, values in which the first detection signal IL1 and the second detection signal IL2 of the left leg detection unit SL, and the third detection signal IR1 and the fourth detection signal IR2 of the right leg detection unit SR are combined, and the like are substituted to the variables X1 to X4. By way of example, four variables, X1, X2, X3, and X4 are used, but four or more variables may be used by combining the first detection signal IL1, the second detection signal IL2, the third detection signal IR1, and the fourth detection signal IR2. The evaluation unit 70 divides one walking cycle into a plurality of movement phases to carry out the movement determination based on the processing result of the computation unit 61. The plurality of movement phases include, for example, a first movement phase OP1, a second movement phase OP2, and a third movement phase OP3. The values of the variables X1 to X4 in equation (1) are characteristic values of the first detection signal IL1, the second detection signal IL2, the third detection signal IR1, and the fourth detection signal IR2 in the first movement phase OP1, the second movement phase OP2, and the third movement phase OP3. The characteristic value is, for example, a continuously obtained value such as a movement average value, a differential value, a value (e.g., X1−X4, X1+X2) calculated by performing a predetermined computation with other characteristic values, and the like. The values of the coefficients a to d in the equation (1) can be changed when setting the different movement phases.

The values of the coefficients a to d and the constant C are set using a discriminant analytical method, which is one method of a multivariate analytical method. For example, the variables X1 to X4 in each of the first movement phase OP1, the second movement phase OP2, and the third movement phase OP3 are calculated based on the result of the walking test conducted beforehand on a plurality of subjects. In the detection of the first movement phase OP1, the second movement phase OP2, and the third movement phase OP3 of the walking test, for example, a different sensor (pressure sensor, etc.) is used other than the first left body sensor SL1, the second left body sensor SL2, the first right body sensor SR1, and the second right body sensor SR2. A combination signal Z1 is obtained by substituting the variables X1 to X4 to the equation (1) set based on the discriminant analytical method. Representing the combination signal Z1 on one graph, the characteristic values in all the movement phases form a group. The coefficients a to d are set to indicate a boundary of the characteristic values of each of the first movement phase OP1, the second movement phase OP2, and the third movement phase OP3 grouped in the graph. That is, the coefficients a to d are set as different values when setting the different movement phases. The constant C is used to adjust the value of the combination signal Z1. The combination signal Z1 set in such manner indicates a predetermined value (e.g., Z1=0) at the boundary of the first movement phase OP1, the second movement phase OP2, and the third movement phase OP3. The computation unit 61 outputs the first detection signal IL1, the second detection signal IL2, the third detection signal IR1, the fourth detection signal IR2, and the combination signal combining the same to the evaluation unit 70.

Figure 6:
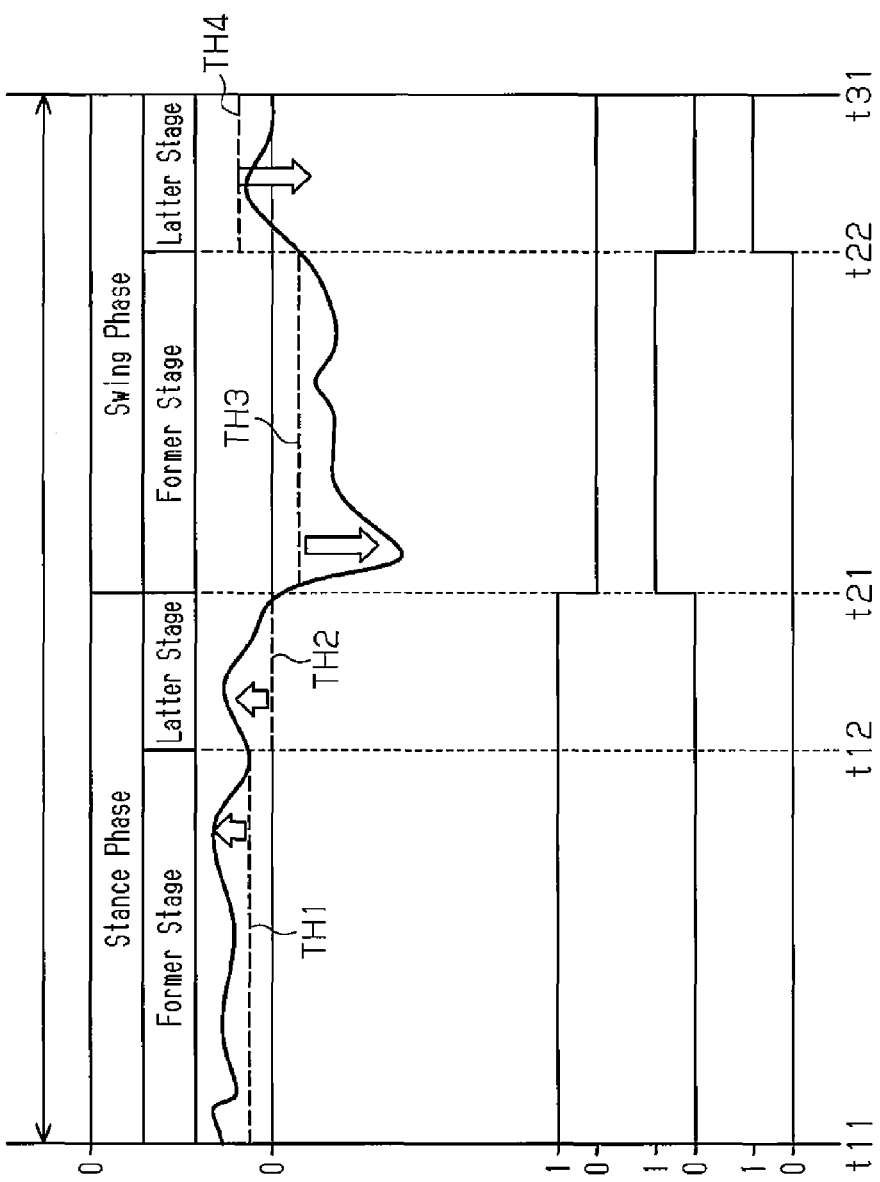
FIGS. 6A to 6F are graphs showing a relationship of the signals used in a movement phase determination and the movement phase in the first embodiment of the present invention, where

FIG. 6 shows the movement phases in one walking cycle, and the signals used in the determination of the movement phases.

The evaluation unit 70 compares the combination signal Z1 shown in FIG. 6C and a predetermined first threshold TH1, a second threshold TH2, a third threshold TH3, and a fourth threshold TH4 with a comparison unit 71 in each movement phase. The first threshold TH1, the second threshold TH2, the third threshold TH3, and the fourth threshold TH4 have different values in each movement phase. The evaluation unit 70 uses the comparison unit 71 and the logical operation unit 81 to carry out a determination on the first detection signal IL1, the second detection signal IL2, the third detection signal IR1, the fourth detection signal IR2, the combination signal, and the like processed by the computation unit 61. The evaluation unit 70 thereby detects the plurality of movement phases shown in FIG. 6, that is, the first movement phase OP1, the second movement phase OP2, and the third movement phase OP3 from the walking movement of one walking cycle shown in FIG. 4. When determining that the movement phase switched with the walking movement, the evaluation unit 70 provides a movement phase number OPN indicating the first movement phase OP1, the second movement phase OP2, and the third movement phase OP3 and a signal indicating that the movement phase is switched.

The measurement unit 72 measures a movement phase duration time tOP, which is a respective duration time of the first movement phase OP1, the second movement phase OP2, and the third movement phase OP3 determined by the evaluation unit 70. The measurement unit 72 stores the measurement result.

The still evaluation unit 73 determines that the walking movement of the user 200 is still if the first movement phase OP1, the second movement phase OP2, and the third movement phase OP3 are continued for longer than or equal to a predetermined time in the walking movement of the user 200. The time setting unit 63 receives an input of a still determination time tREF used in the walking still state determination. The still evaluation unit 73 compares the movement phase duration time tOP stored in the measurement unit 72 and the still determination time tREF input to the time setting unit 63. The still evaluation unit 73 determines that the walking movement is still if the movement phase duration time tOP is longer than the still determination time tREF of the time setting unit 63. The still evaluation unit 73 outputs the determination result to the stimulus applying control unit 62.

The stimulus applying control unit 62 controls the left body stimulus applying unit 90L attached to the first attachment unit 10L and the right body stimulus applying unit 90R attached to the second attachment unit 10R based on the determination result provided from the still evaluation unit 73.

The display unit 43 displays the determination result, and the like of the walking state of the user 200 in the first movement phase OP1, the second movement phase OP2, and the third movement phase OP3, for example. The display unit 43 displays the difference in the movement of the left and right legs of the first movement phase OP1, the second movement phase OP2, and the third movement phase OP3, and the evaluation result of the walking movement based on the difference in the movement of the left and right legs. The target of the movement displayed on the display unit 43 can be changed by the user 200 using the operation unit 44.

The power supply unit 41 supplies a drive current to the stimulation device main body unit 40. The power supply unit 41 supplies the drive current to the first attachment unit 10L and the second attachment unit 10R. The power supply unit 41, for example, is a power supply circuit that generates a required drive current by a power supply from a chargeable battery, a dry cell battery, and a commercial power supply, for example.

Figure 7:
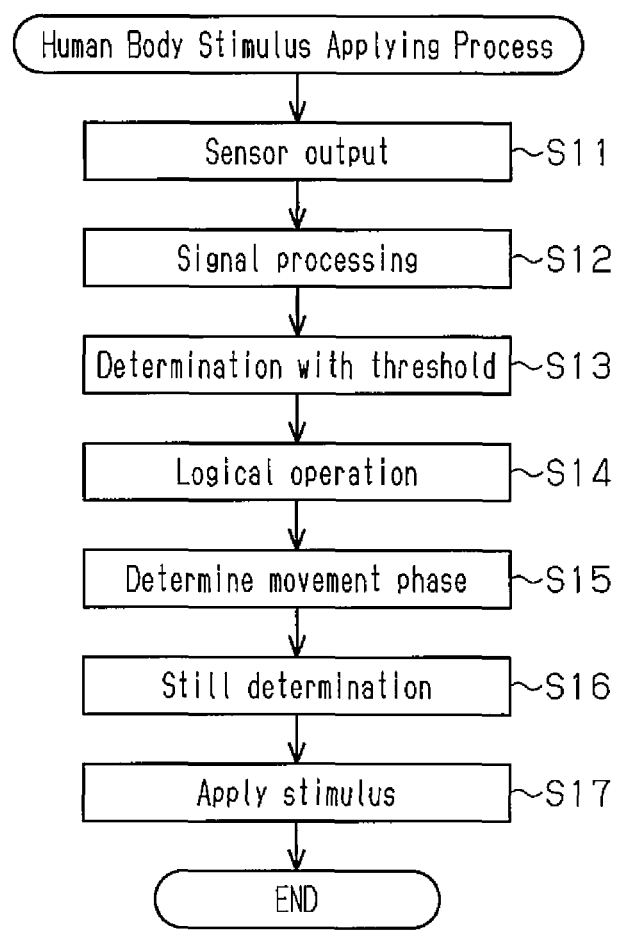
FIG. 7 is a flowchart showing a human body stimulus applying process executed by the control unit of the first embodiment of the present invention.

The operation of the human body stimulus applying process executed by the control unit 60 of the human body stimulus applying device 1 will now be described according to a flowchart shown in FIG. 7.

When the user 200 carries out the walking movement, the first left body sensor SL1, the second left body sensor SL2, the first right body sensor SR1, and the second right body sensor SR2 detect the displacement of the physical quantity of the left leg 210L and the right leg 210R of the user 200 involved in the walking movement in step S11. The first left body sensor SL1, the second left body sensor SL2, the first right body sensor SR1, and the second right body sensor SR2 generate the first detection signal IL1, the second detection signal IL2, the third detection signal IR1, and the fourth detection signal IR2 indicating the detection result, and output the detection signals to the computation unit 61.

In step S12, the computation unit 61 carries out the process of combining the first detection signal IL1 and the third detection signal IR1, and the second detection signal IL2 and the fourth detection signal IR2 of the first left body sensor SL1, the second left body sensor SL2, the first right body sensor SR1, and the second right body sensor SR2 dividedly arranged by the reference plane 200C. The computation unit 61 also carries out the signal processing with respect to the combined signal and the signals before being combined. The computation unit 61 outputs the signal generated by the signal processing to the evaluation unit 70.

In step S13, the evaluation unit 70 compares the threshold for dividing one walking cycle for every property of the walking movement, and the signal generated by the signal processing. The evaluation unit 70 detects a plurality of the first movement phase OP1, the second movement phase OP2, and the third movement phase OP3 from the one walking cycle based on the comparison result. The evaluation unit 70 separates the one walking cycle into the first movement phase OP1 included in the stance phase and the second movement phase OP2 and the third movement phase OP3 included in the swing phase shown in FIG. 6. In the example shown in FIG. 6, the stance phase includes only one zone of the first movement phase OP1. The evaluation unit 70 causes the comparison unit 71 to compare, for example, the combination signal Z1 shown in FIG. 6C as the subtraction result of the first detection signal IL1 and the third detection signal IR1, and the defined first threshold TH1, the second threshold TH2, the third threshold TH3, and the fourth threshold TH4. The evaluation unit 70 determines the zone in which the combination signal Z1 exceeds the first threshold TH1 or the second threshold TH2 as the stance phase based on the comparison result. The comparison unit 71 outputs a comparison signal "1" (high level) when the combination signal Z1 is smaller than the first threshold TH1 to the fourth threshold TH4. The comparison unit 71 outputs a comparison signal "0" (low level) when the combination signal Z1 is greater than the first threshold TH1 to the fourth threshold TH4. Each of the first threshold TH1, the second threshold TH2, the third threshold TH3, and the fourth threshold TH4 has a constant value in the one walking cycle.

In step S14, the logical operation unit 81 of the walking phase dividing unit 80 carries out the logical operation of the comparison signal input from the comparison unit 71.

In step S15, the evaluation unit 70 determines the first movement phase OP1, the second movement phase OP2, and the third movement phase OP3 based on the output result of the logical operation unit 81. The walking phase dividing unit 80 determines the zone of t11 to t12, in which the combination signal Z1 exceeds the first threshold TH1, in the stance phase as the former stage of the stance phase. The walking phase dividing unit 80 determines the zone after the combination signal Z1 once becomes smaller than or equal to the first threshold TH1, the zone being the zone of t12 to t21 in which the combination signal Z1 exceeds the second threshold TH2, as the latter stage of the stance phase. The evaluation unit 70 defines the zone of t11 to t21 including the zone of t11 to t12 determined as the former stage of the stance phase and the zone of t12 to t21 determined as the latter stage of the stance phase as the first movement phase OP1 based on the determination result of the walking phase dividing unit 80. The former stage of the stance phase is the zone from when the heel of one foot touches the ground until the heel moves away from the ground during the one walking cycle. The latter stage of the stance phase is the zone from when the heel of one foot moves away from the ground until the toe moves away from the ground during the one walking cycle.

The walking phase dividing unit 80 determines the zone following the latter stage of the stance phase, the zone being the zone of t21 to t22 in which the combination signal Z1 becomes smaller than or equal to the third threshold TH3, as the former stage of the swing phase. The walking phase dividing unit 80 determines the zone following the former stage of the swing phase, the zone being the zone of t22 to t31 in which the combination signal Z1 becomes greater than the third threshold TH3 and smaller than or equal to the threshold TH4, as the latter stage of the swing phase. The evaluation unit 70 defines the former stage of the swing phase as the second movement phase OP2 and the latter stage of the swing phase as the third movement phase OP3 based on the determination result of the walking phase dividing unit 80. In the walking phase dividing unit 80, after the one walking cycle is divided into a plurality of zones, the plurality of divided zones may be coupled. For example, when the target movement phase is the swing phase, the swing phase may be divided into a plurality of zones, and the plurality of divided zones may be coupled.

In step S16, the still evaluation unit 73 determines the walking still state of the user 200. The still evaluation unit 73 determines the walking still state using the respective duration times of the first movement phase OP1, the second movement phase OP2, and the third movement phase OP3 determined by the evaluation unit 70.

The left body stimulus applying unit 90L and the right body stimulus applying unit 90R apply stimulus at a predetermined timing on the user 200 if the still evaluation unit 73 does not determine that the walking movement is still. The left body stimulus applying unit 90L and the right body stimulus applying unit 90R change the magnitude of the stimulus application on the user 200 if the still evaluation unit 73 determines that the walking movement is still. Specifically, the left body stimulus applying unit 90L and the right body stimulus applying unit 90R weaken the stimulating power or stop the stimulus application if the still evaluation unit 73 determines that the walking movement is still.

In the determination using the thresholds, the logical operation, and the movement phase determination in step S13 to step S15, the same movement phase may be determined over plural times within one walking cycle. In this case, the walking phase dividing unit 80 separately acquires the determination signal that differs from the determination signal used in the determination. The evaluation unit 70 specifies the first movement phase OP1, the second movement phase OP2, and the third movement phase OP3 by carrying out the logical operation on the separately acquired determination signal.

The first threshold TH1, the second threshold TH2, the third threshold TH3, and the fourth threshold TH4 are, for example, set based on the result of the walking test conducted beforehand on a plurality of subjects. The walking test is conducted, for example, by providing a different sensor (e.g., pressure sensor) on the body of the subject in addition to the first left body sensor SL1, the second left body sensor SL2, the first right body sensor SR1, and the second right body sensor SR2. Such different sensor is arranged to detect the first movement phase OP1, the second movement phase OP2, and the third movement phase OP3 in the walking test. For example, the pressure sensor arranged on the back of the foot detects a period in which the foot is touching the ground in the one walking cycle. The tester defines the period in which the foot is detected to be touching the ground as the stance phase, that is, the first movement phase OP1. The tester uses the first movement phase OP1, the second movement phase OP2, and the third movement phase OP3 detected with the different sensor to acquire the value of the combination signal of the first detection signal IL1, the second detection signal IL2, the third detection signal IR1, and the fourth detection signal IR2 of each subject. Thus, for example, the average value of the values of the combination signals at the boundaries of the first movement phase OP1, the second movement phase OP2, and the third movement phase OP3 is calculated, and the result is set as the first threshold TH1, the second threshold TH2, the third threshold TH3, and the fourth threshold TH4. For example, the second threshold TH2 is set with a value that determines the latter stage of the stance phase, and the zone (former stage of the stance phase and the former stage of the swing phase) before and after thereof with respect to the combination signal, as shown in FIG. 6. That is, the second threshold TH2 is set from the average value of the values of the combination signals at the boundaries of the former stage of the stance phase and the zone before and after thereof of a plurality of subjects in the walking test. The first threshold TH1, the second threshold TH2, the third threshold TH3, and the fourth threshold TH4 are not limited to the values of the boundaries. For example, the value may be set based on the average value of the values of the combination signals in the entire movement phase of each of the first movement phase OP1, the second movement phase OP2, and the third movement phase OP3.

A flowchart of the walking still determination process will be described with reference to FIG. 8.

When the operation of the human body stimulus applying device 1 is started, the control unit 60 executes step S21 to step S23, which are initial setting steps.

In step S21, the time setting unit 63 sets the value of the determination time used for the walking still state determination as the still determination time tREF.

In step S22, the measurement unit 72 sets the movement phase duration time tOP stored in the measurement unit 72 to zero.

In step S23, the evaluation unit 70 sets the previous movement phase number OPN (n−1) used in the walking cycle time measurement to zero.

In step S24, the evaluation unit 70 determines the movement phase.

In step S25, the evaluation unit 70 sets the movement phase number OPN(n) of the determined movement phase.

In step S26, the measurement unit 72 determines whether the movement phase number OPN(n) determined in step S25 matches the previous movement phase number OPN(n−1). The measurement unit 72 determines whether or not the movement determined to have the same movement phase number is continuing by executing step S26.

If determined that the movement phase number OPN(n) matches the previous movement phase number OPN(n−1) (Yes) in step S26, the measurement unit 72 adds one to the movement phase duration time tOP stored in the measurement unit 72 in step S27.

If determined that the movement phase number OPN(n) does not match the previous movement phase number OPN (n−1) (No) in step S26, the measurement unit 72 resets the movement phase duration time tOP stored in the measurement unit 72 and sets the movement phase duration time tOP to zero in step S28.

In step S29, the still evaluation unit 73 compares the movement phase duration time tOP and the still determination time tREF.

If determined that the movement phase duration time tOP is longer than the still determination time tREF (Yes) in step S29, the stimulus applying control unit 62 sets the control flag FLG to one in step S30.

If determined that the movement phase duration time tOP is not longer than the still determination time tREF (No) in step S29, the stimulus applying control unit 62 resets the control flag FLG and sets the control flag FLG to zero in step S31.

In step S32, the evaluation unit 70 sets the determined movement phase number OPN(n) to OPN(n−1) as the previous movement phase number.

In step S33, the control unit 60 sets the waiting time of 10 ms. The waiting time is a determining cycle of determining the movement phase in step S24. When the waiting time is set to 10 ms, the evaluation unit 70 determines the movement phase at an interval of 10 ms. The waiting time is set to an optimum value according to the walking cycle.

The control unit 60 repeats steps S24 to S33 during a period the human body stimulus applying device 1 is carrying out the operation.

Figure 8:
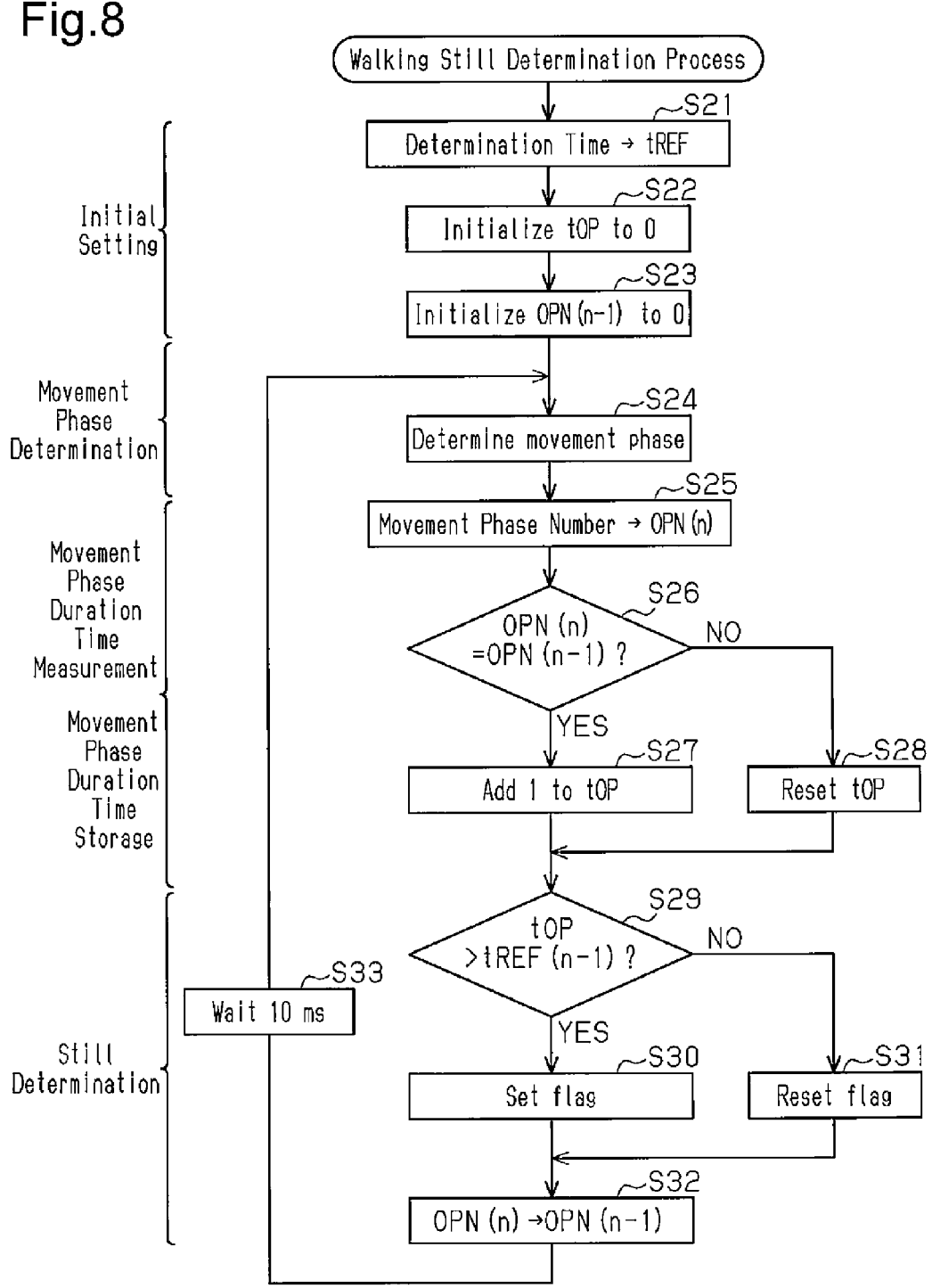
FIG. 8 is a flowchart showing a walking still determination process executed by an evaluation unit of the first embodiment of the present invention.

The measurement unit 72 measures the duration time of the movement phase determined by the evaluation unit 70 in step S27 as the number of counts of the time having 10 ms as a unit by executing the flowchart shown in FIG. 8.

The still evaluation unit 73 determines that the walking movement is still if the movement phase duration time tOP measured by the measurement unit 72 is longer than the still determination time tREF in step S29.

The measurement unit 72 sets the movement phase duration time tOP stored in the measurement unit 72 to zero when the movement phase number OPN(n) determined by the evaluation unit 70 changed from the previous movement phase number OPN(n−1) in step S28.

The stimulus applying control unit 62 controls the left body stimulus applying unit 90L and the right body stimulus applying unit 90R based on the value of the control flag FLG to change the magnitude of the stimulus to apply on the user 200. That is, while the walking movement is determined as still in step S29 and the control flag FLG is set to one in step S30, the left body stimulus applying unit 90L and the right body stimulus applying unit 90R weaken the stimulating power on the user 200 or stop the stimulus application.

An operation of the human body stimulus applying device 1 will now be described.

The human body stimulus applying device 1 described above includes the first left body sensor SL1 and the second left body sensor SL2 arranged on the left leg 210L of the user 200, and the first right body sensor SR1 and the second right body sensor SR2 arranged on the right leg 210R of the user 200. The first left body sensor SL1, the second left body sensor SL2, the first right body sensor SR1, and the second right body sensor SR2 detect the bilaterally symmetric walking movement. The evaluation unit 70 combines the first detection signal IL1, the second detection signal IL2, the third detection signal IR1, and the fourth detection signal IR2 generated by the first left body sensor SL1, the second left body sensor SL2, the first right body sensor SR1, and the second right body sensor SR2 to determine the walking movement of the user 200. The evaluation unit 70 includes the walking phase dividing unit 80. The walking movement is determined by dividing the stance phase and the swing phase within the one walking cycle into a plurality of movement phases. The still evaluation unit 73 carries out the walking still state determination on the basis of the measurement result obtained by measuring the duration time of the movement phase. Therefore, the human body stimulus applying device 1 can carry out the walking still state determination in each movement phase. Thus, the state in which the walking movement is still can be appropriately detected. Furthermore, the walking still state determination can be carried out in a short period of time while reducing erroneous determinations. The stimulus applying control unit 62 controls the left body stimulus applying unit 90L and the right body stimulus applying unit 90R based on the determination result of the still evaluation unit 73. Thus, an appropriate stimulus applying control can be carried out.

The measurement unit 72 measures the duration time of the movement phase with respect to each of the plurality of movement phases. The still evaluation unit 73 carries out the walking still state determination with respect to each of the plurality of movement phases. The stimulus applying control unit 62 controls the left body stimulus applying unit 90L and the right body stimulus applying unit 90R based on the determination result of the still evaluation unit 73. Therefore, a highly accurate walking still state determination can be carried out in a short period of time. Thus, a highly accurate stimulus applying control can be carried out.

The first left body sensor SL1 and the second left body sensor SL2, and the first right body sensor SR1 and the second right body sensor SR2 are respectively arranged in the two regions on both sides of the reference plane 200C of the user. The first left body sensor SL1, the second left body sensor SL2, the first right body sensor SR1, and the second right body sensor SR2 detect the bilaterally symmetric walking movement. The evaluation unit 70 combines the first detection signal IL1, the second detection signal IL2, the third detection signal IR1, and the fourth detection signal IR2 generated by the first left body sensor SL1, the second left body sensor SL2, the first right body sensor SR1, and the second right body sensor SR2 to determine the walking movement of the user 200. The evaluation unit 70 includes the walking phase dividing unit 80. The walking movement is determined by dividing the stance phase and the swing phase within the one walking cycle into a plurality of movement phases. The still evaluation unit 73 carries out the walking still state determination on the basis of the measurement result obtained by measuring the duration time of the movement phase. Therefore, the highly accurate walking still state determination can be carried out.

Even when evaluating the balance of the regions of the user positioned in two regions on both sides of the reference plane 200, for example, the left and right legs of the user, the evaluation including the state of the other leg can be carried out. For example, when evaluating one leg, the evaluation including the interaction with the state of the other leg can be carried out for such evaluation.

The first left body sensor SL1, the second left body sensor SL2, and the first right body sensor SR1, the second right body sensor SR2 are arranged at symmetrical positions with respect to the reference plane 200C, which becomes the boundary of the walking movement carried out bilaterally symmetrically. That is, the human body often moves parallel to the reference plane 200 that evenly divides the human body seen from the walking direction. The movement of the human body has a strong tendency of being mutually similar in the two regions (e.g., left limb, right limb) divided by the reference plane 200. For example, in the movement of sitting on a chair, the left and right legs are simultaneously moved such as, mainly, the left and right knees are stretched from the standing state, and then the knees are bent when close to the sitting surface, and the like. The evaluation unit 70 uses the signal in which the first detection signal IL1, the second detection signal IL2, the third detection signal IR1, and the fourth detection signal IR2 are combined to carry out the movement determination based on the movement of a plurality of regions of the human body that are simultaneously moved. Therefore, the amount of data used for the movement determination by the evaluation unit 70 is doubled with respect to the configuration of using only the first detection signal IL1 and the second detection signal IL2 of the first left body sensor SL1 and the second left body sensor SL2. Thus, the walking movement of the user is more accurately determined, and the more accurate walking still state determination can be carried out.

In the movement of the human body, a phase difference is sometimes shifted by about 180 degrees between the left region and the right region as in the movement of the hip side surface when walking. Even when the determination of the movement is difficult from the detection results of the first left body sensor SL1 and the second left body sensor SL2, which are one sensor, the evaluation unit 70 in the human body stimulus applying device 1 can use the detection results of the first right body sensor SR1 and the second right body sensor SR2, which are the other sensor. Thus, even in the movement in which the determination is conventionally difficult, the determination is facilitated. A more accurate walking still state determination thus can be carried out.

The human body stimulus applying device 1 includes the first left body sensor SL1 and the second left body sensor SL2 attached to one limb portion of the user 200, and the first right body sensor SR1 and the second right body sensor SR2 attached to the other limb portion of the user 200. The variation of the detection signal becomes greater by attaching the first left body sensor SL1, the second left body sensor SL2, the first right body sensor SR1, and the second right body sensor SR2 to the left and right limbs of the human body than by attaching the sensors to the hip of the user 200. The acquirable amount of data thus increases. In the method for carrying out the movement determination by the difference of the sensor detection signal values between the reference posture state and the movement state, the signal used in the movement determination is a difference of the sensor detection signal values between the reference posture state and the movement state, and is a small value. The highly accurate movement determination is thus difficult with such method. On the contrary, the sensor detection signals of the first left body sensor SL1 and the second left body sensor SL2 and the first right body sensor SR1 and the second right body sensor SR2 respectively attached to the left and right limb portions have a sufficient difference with each other. The evaluation unit 70 thus can carry out the movement determination more accurately, and can carry out the highly accurate walking still state determination.

The human body stimulus applying device 1 has the first left body sensor SL1, the second left body sensor SL2, the first right body sensor SR1, and the second right body sensor SR2 arranged at positions crossing over the knees of the user. The first left body sensor SL1, the second left body sensor SL2, the first right body sensor SR1, and the second right body sensor SR2 are configured such that a turning position (angular speed, etc.) of the knee joint can be detected. For example, in the former stage of the swing phase, the femoral region turns with the hip joint as the center in the same direction as the advancing direction.

The first left body sensor SL1 and the first right body sensor SR1 (angular speed sensor) detect the acceleration of the femoral region with respect to the turning direction, and generate the first detection signal IL1 and the third detection signal IR1 indicating the detected acceleration. The leg region turns in a direction the inertia force acts with the knee joint as the center. The second left body sensor SL2 and the second right body sensor SR2 (angular speed sensor) detect the angular speed of the leg region along the turning direction, and generate the second detection signal IL2 and the fourth detection signal IR2 indicating the detected angular speed. In the latter stage of the swing phase, the femoral region and the leg region turn in opposite directions from the former stage of the swing phase. The first left body sensor SL1, the second left body sensor SL2, the first right body sensor SR1, and the second right body sensor SR2 are arranged in the regions crossing over the knee joints to detect the characteristic movement of the feet in the swing phase. Thus, the detection accuracy of the second movement phase OP2 and the third movement phase OP3 can be enhanced, and a highly accurate walking still state determination can be carried out.

The human body stimulus applying device 1 has the following advantages.

(1) The human body stimulus applying device 1 includes the first left body sensor SL1, the second left body sensor SL2, the first right body sensor SR1, and the second right body sensor SR2 as detection units. The human body stimulus applying device 1 includes the evaluation unit 70 that combines the first detection signal IL1, the second detection signal IL2, the third detection signal IR1, and the fourth detection signal IR2 generated in each of the first left body sensor SL1, the second left body sensor SL2, the first right body sensor SR1, and the second right body sensor SR2 to determine the movement of the human body. The evaluation unit 70 includes the walking phase dividing unit 80, and carries out the movement determination by dividing the stance phase and the swing phase within one walking cycle at the time of the walking movement of the user 200 into a plurality of movement phases. The still evaluation unit 73 measures the duration time of the movement phase, and carries out the walking still state determination. The stimulus applying control unit 62 controls the left body stimulus applying unit 90L and the right body stimulus applying unit 90R based on the determination result of the still evaluation unit 73. According to such configuration, the state in which the walking movement is still is appropriately detected. The walking still state determination is carried out in a short period of time while reducing erroneous determinations. Thus, an appropriate stimulus applying control is carried out.

(2) The evaluation unit 70 includes the walking phase dividing unit 80, and carries out the movement determination by dividing the stance phase and the swing phase within one walking cycle at the time of the walking movement of the user 200 into a plurality of movement phases. The evaluation unit 70 includes the measurement unit 72. The measurement unit 72 measures the duration time in the respective movement phases. The measurement unit 72 stores the measurement result. The still evaluation unit 73 carries out the walking still state determination with respect to each of the plurality of movement phases. The stimulus applying control unit 62 controls the left body stimulus applying unit 90L and the right body stimulus applying unit 90R based on the determination result of the still evaluation unit 73. According to such configuration, a highly accurate walking still state determination is carried out in a short period of time. Thus, a highly accurate stimulus applying control is carried out.

(3) The human body stimulus applying device 1 includes the first left body sensor SL1 and the second left body sensor SL2 configuring the left leg detection unit SL and the first right body sensor SR1 and the second right body sensor SR2 configuring the right leg detection unit SR at symmetrical positions with respect to the reference plane 200C of the user 200. The evaluation unit 70 combines the first detection signal IL1, the second detection signal IL2, the third detection signal IR1, and the fourth detection signal IR2 indicating the detection results by the left leg detection unit SL and the right leg detection unit SR to determine the movement of the user 200. The still evaluation unit 73 carries out the walking still state determination based on the determination result of the evaluation unit 70. According to such configuration, the amount of data used for the determination of the walking movement is increased and a highly accurate walking still state determination is carried out.

(4) In the human body stimulus applying device 1, the plane of the center of the body that divides the human body seen from the walking direction evenly to the left and right is the reference plane 200C. The first left body sensor SL1 and the first right body sensor SR1, and the second left body sensor SL2 and the second right body sensor SR2 are symmetrically arranged with each other with respect to the reference plane 200C. According to such configuration, the amount of data of the signal input to the evaluation unit 70 is doubled with respect to the configuration in which only the first detection signal IL1 of the first left body sensor SL1 and the second detection signal IL2 of the second left body sensor SL2 are used, so that the walking movement of the user 200 is more accurately determined. Thus, the walking still state determination is accurately carried out.

(5) The left body detector 50L of the human body stimulus applying device 1 includes the first left body sensor SL1 and the second left body sensor SL2 arranged on one limb portion of the human body. The right body detector 50R of the human body stimulus applying device 1 includes the first right body sensor SR1 and the second right body sensor SR2 arranged on the other limb portion of the human body. According to such configuration, the human body stimulus applying device 1 acquires, for example, greater amount of signals indicating the displacement of the human body involved in various types of movements such as the walking movement, and the like. Thus, the human body stimulus applying device 1 carries out the movement determination based on abundant data indicating the movement of the human body. The movement determination is thus carried out in more detail and with high accuracy. The walking still state determination is carried out in more detail and with high accuracy.

The human body stimulus applying device 1 combines the detection signals of the first left body sensor SL1, the second left body sensor SL2, the first right body sensor SR1, and the second right body sensor SR2 attached at symmetrical positions with respect to the reference plane 200C. The human body stimulus applying device 1 carries out the movement determination of one limb of the human body based on the combination signal. According to such configuration, the movement is rapidly determined with high accuracy. The walking still state determination is thus carried out with higher speed and higher accuracy.

Second Embodiment

The human body stimulus applying device 1 of the second embodiment has a configuration different in the following portions compared to the human body stimulus applying device 1 of the first embodiment, and the same configuration in other portions. The same reference numerals are denoted on the configurations common with the human body stimulus applying device 1 of the first embodiment, and the description thereof will be partially or entirely omitted.

The human body stimulus applying device 1 of the first embodiment includes the time setting unit 63 that receives an input of the still determination time tREF. The human body stimulus applying device 1 of the second embodiment, on the other hand, includes a time setting unit 64 that sets the still determination time tREF based on the measurement value of the measurement unit 72.

Figure 9:
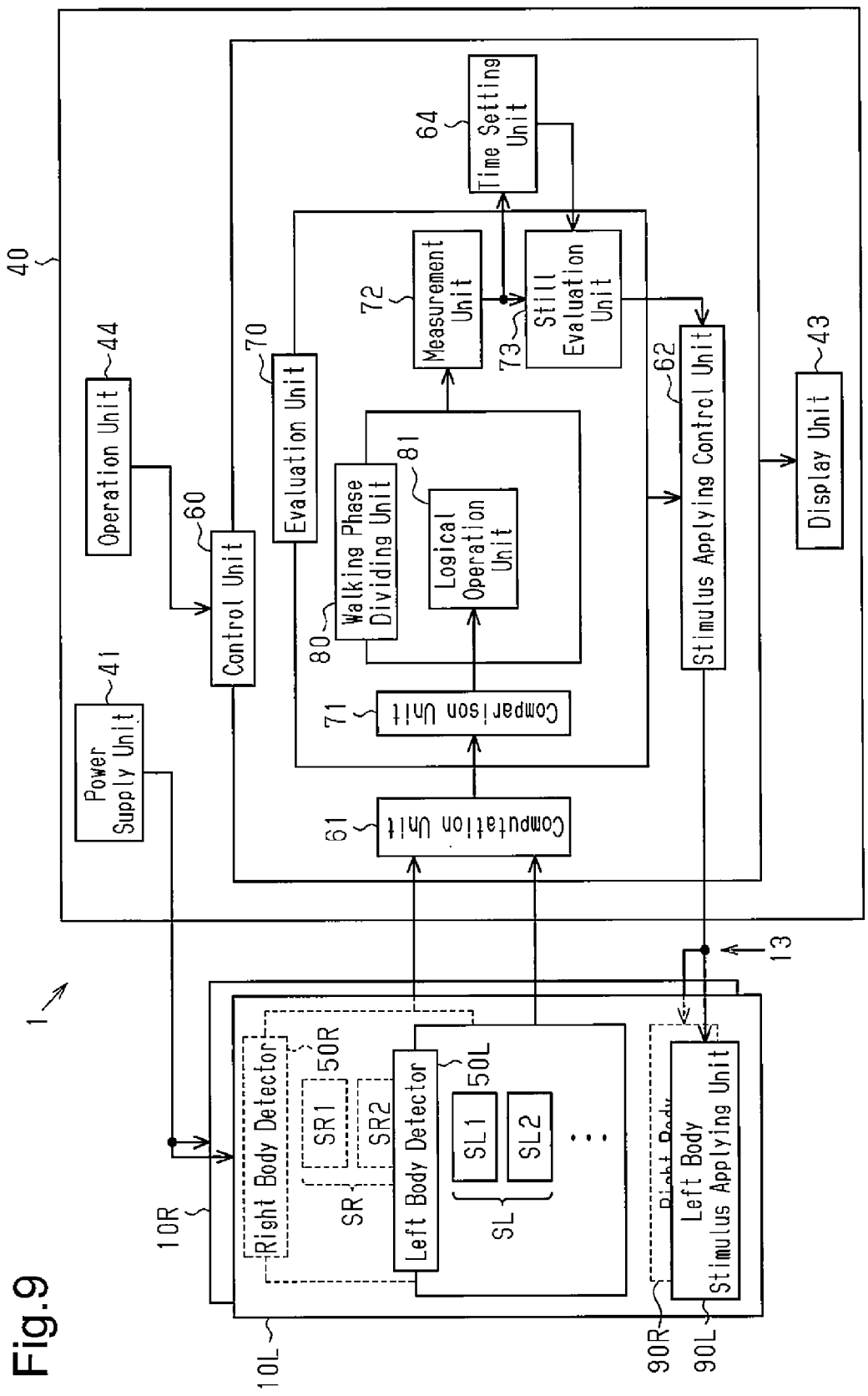
FIG. 9 is a circuit block configuration diagram of the human body stimulus applying device according to a second embodiment of the present invention.

A configuration of the human body stimulus applying device 1 will now be described with reference to FIG. 9.

The human body stimulus applying device 1 includes the time setting unit 64. The measurement unit 72 measures the respective movement phase duration times tOP of the first movement phase OP1, the second movement phase OP2, and the third movement phase OP3 determined by the evaluation unit 70. The measurement unit 72 stores the measurement result. The time setting unit 64 sets the still determination time tREF. The still evaluation unit 73 compares the movement phase duration time tOP stored in the measurement unit 72 and the still determination time tREF set by the time setting unit 64. The still evaluation unit 73 determines that the walking movement is still when the movement phase duration time tOP is longer than the still determination time tREF set by the time setting unit 64. The still evaluation unit 73 outputs the determination result to the stimulus applying control unit 62.

The time setting unit 64 includes a determination time defining unit. The determination time defining unit defines the still determination time tREF based on the result of the walking test conducted beforehand on a plurality of subjects. The time setting unit 64 sets the still determination time tREF based on the definition of the determination time defining unit.

The definition of the still determination time by the determination time defining unit will be described with reference to FIG. 10.

The stance phase in the walking movement of the human body is about 60% of the one walking cycle, and it is known that one walking cycle time and the duration time of each movement phase are correlated. A person whose one walking cycle is long is also known to have a long duration time in each movement phase. Thus, the still determination time tREF needs to be changed in accordance with the walking property of the user 200 of the human body stimulus applying device 1 in order to accurately carry out the walking still state determination.

Figure 10A:
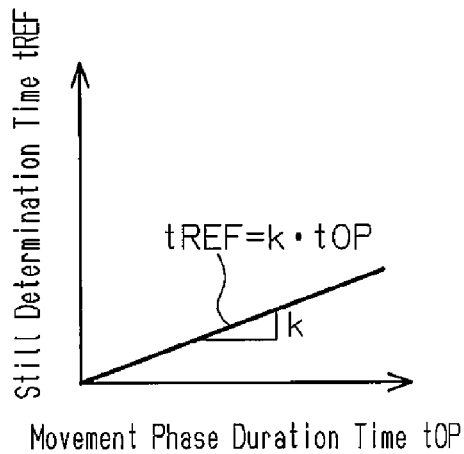
FIGS. 10A, 10B, and 10C are views showing different setting methods with respect to the setting of the still determination time in the second embodiment of the present invention.

FIG. 10A is a graph showing a method of setting the still determination time tREF by multiplying a positive proportionality coefficient with respect to the movement phase duration time tOP. The determination time defining unit defines the still determination time tREF, which is an output value, using a proportionality coefficient k with respect to the movement phase duration time tOP, which is an input value. In other words, the still determination time tREF is determined by the following equation.

$$tREF = k \cdot tOP$$

The determination time defining unit defines the still determination time tREF using the proportionality coefficient k shown in FIG. 10A based on at least one duration time of the duration times of the plurality of divided walking phases measured by the measurement unit 72 before the current walking cycle. The time setting unit 64 holds the result of the walking test conducted beforehand on the plurality of subjects in the storage unit. The determination time defining unit defines the still determination time tREF with reference to the result of the walking test from the measurement time of the measurement unit 72. The still evaluation unit 73 can carry out the walking still state determination in a short period of time.

Figure 10B:
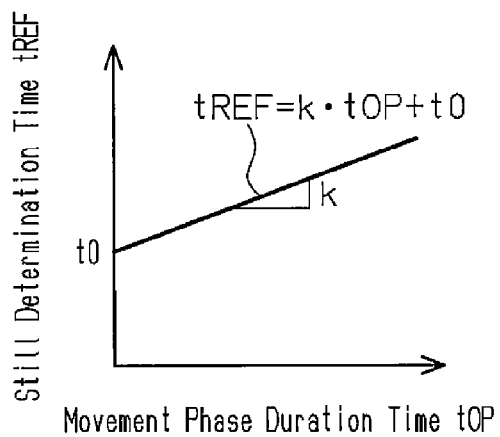

FIG. 10B is a graph showing a method of setting the still determination time tREF by multiplying the positive proportionality coefficient with respect to the movement phase duration time and adding an offset value t0.

The determination time defining unit defines the still determination time tREF using the proportionality coefficient k and the offset value t0 with respect to the movement phase duration time tOP. In other words, the still determination time tREF is determined by the following equation.

$$tREF = k \cdot tOP + 0$$

The still evaluation unit 73 can reduce erroneous operations caused by noise, and the like, and carry out a stable walking still state determination even when the movement phase duration time tOP is short.

Figure 10C:
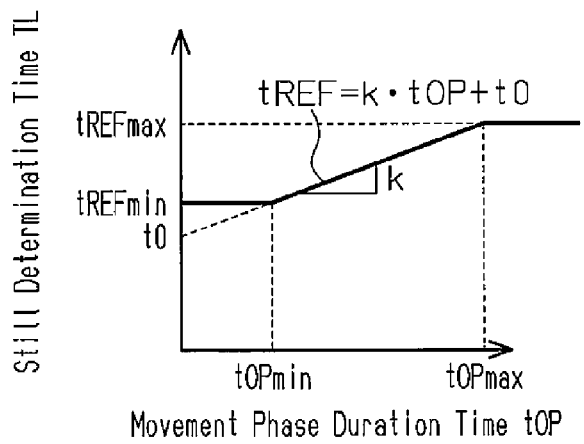

FIG. 10C is a graph showing a method for setting the still determination time tREF by multiplying the positive proportionality coefficient with respect to the movement phase duration time TOP, adding the offset value t0, and using a determination minimum time tREFmin and a determination maximum time tREFmax. The minimum duration time tOPmin and the maximum duration time tOPmax of the movement phase duration time tOP are set based on the result of the walking test conducted beforehand on a great number of subjects. The determination minimum time tREFmin and the determination maximum time tREFmax of the still determination time tREF are set in correspondence with the minimum duration time tOPmin and the maximum duration time tOPmax. The determination time defining unit assumes that the movement phase having the duration time of smaller than or equal to the minimum duration time tOPmin as a jump movement, and the like other than the walking movement, and defines that the still determination time tREF is the determination minimum time tREFmin. The determination time defining unit assumes that the movement phases having the duration time of greater than or equal to the maximum duration time tOPmax are all walking still states, and defines that the still determination time tREF is the determination maximum time tREFmax. The still evaluation unit 73 can reduce erroneous operations caused by noise, and the like and carry out the stable walking still state determination even when the movement phase duration time tOP is short. The still evaluation unit 73 can reduce the increase in the determination time even when the movement phase duration time tOP is long.

In the setting of the still determination time tREF, the human body stimulus applying device 1 is configured to be able to select the setting methods shown in FIGS. 10A to 10C or other setting methods according to the mode of the walking movement carried out by the user 200. The mode of the walking movement includes walking on a flat road surface, walking on a road surface having a gradient, walking when going up and down the stairs, or other walking modes.

A flowchart of the walking still determining process will be described with reference to FIG. 11.

In steps S41 to S45, the operations similar to steps S21 to S25 described in FIG. 8 in the first embodiment are carried out.

In step S46, the time setting unit 64 sets the still determination time tREF based on at least one duration time of the duration times of the plurality of divided walking phases measured by the measurement unit 72 before the current walking cycle.

In step S47, the measurement unit 72 determines whether the movement phase number OPN(n) determined in step S45 matches the previous movement phase number OPN(n−1). The measurement unit 72 determines whether the movement determined to have the same movement phase number is continuing by executing step S47.

If determined that the movement phase number OPN(n) matches the previous movement phase number OPN(n−1) (Yes) in step S47, the measurement unit 72 adds one to the movement phase duration time tOP stored in the measurement unit 72 in step S48.

If determined that the movement phase number OPN(n) does not match the previous movement phase number OPN (n−1) (No) in step S47, the measurement unit 72 resets the movement phase duration time tOP stored in the measurement unit 72 and sets the movement phase duration time tOP to zero in step S49.

In step S50, the still evaluation unit 73 compares the movement phase duration time tOP with the still determination time tREF.

If determined that the movement phase duration time tOP is longer than the still determination time tREF (Yes) in step S50, the stimulus applying control unit 62 sets the control flag FLG to one in step S51.

If determined that the movement phase duration time tOP is not longer than the still determination time tREF (No) in step S50, the stimulus applying control unit 62 resets the control flag FLG and sets the control flag FLG to zero in step S52.

In step S53, the evaluation unit 70 sets the determined movement phase number OPN(n) to OPN(n−1) as the previous movement phase number.

In step S54, the control unit 60 sets the waiting time of 10 ms. The waiting time is a determining cycle in which the evaluation unit 70 executes the determination, as previously described. The waiting time is set to an optimum value according to the walking cycle.

The control unit 60 repeats steps S44 to S54 during a period the human body stimulus applying device 1 is carrying out the operation.

Figure 11:
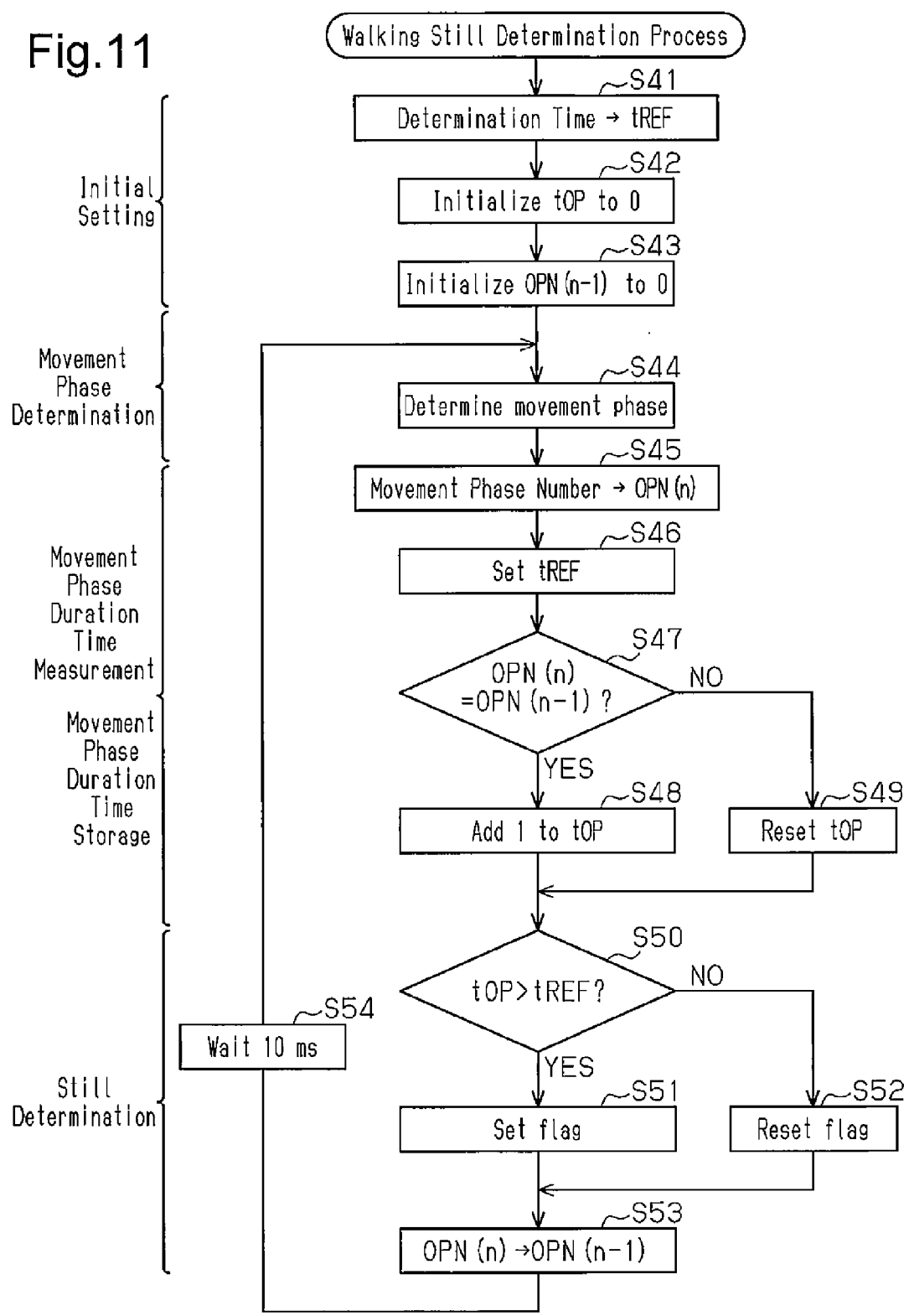
FIG. 11 is a flowchart showing the walking still state determination and the stimulus applying control of the human body stimulus applying device according to the second embodiment of the present invention.

The measurement unit 72 measures the duration time of the movement phase determined by the evaluation unit 70 in step S48 as the number of counts of the time having 10 ms as a unit by executing the flowchart shown in FIG. 11.

The still evaluation unit 73 determines that the walking movement is still if the movement phase duration time tOP measured by the measurement unit 72 is longer than the still determination time tREF in step S50.

The measurement unit 72 sets the movement phase duration time tOP stored in the measurement unit 72 to zero when the movement phase number OPN(n) determined by the evaluation unit 70 changed from the previous movement phase number OPN(n−1) in step S49.

The stimulus applying control unit 62 controls the left body stimulus applying unit 90L and the right body stimulus applying unit 90R based on the value of the control flag FLG to change the magnitude of the stimulus to apply on the user 200. That is, while the walking movement is determined as still in step S29 and the control flag FLG is set to one in step S30, the left body stimulus applying unit 90L and the right body stimulus applying unit 90R weaken the stimulating power on the user 200 or stop the stimulus application.

The operation of the human body stimulus applying device 1 will now be described.

The evaluation unit 70 of the human body stimulus applying device 1 includes the walking phase dividing unit 80. The walking phase dividing unit 80 divides the stance phase and the swing phase within one walking cycle into a plurality of movement phases, and carries out the movement determination. The measurement unit 72 measures the movement phase duration time tOP with respect to each of the movement phases divided into plurals. The time setting unit 64 includes a determination time defining unit. The determination time defining unit defines the still determination time tREF based on at least one duration time of the duration times of the plurality of divided walking phases measured by the measurement unit 72 before the current walking cycle. The time setting unit 64 sets the still determination time tREF based on the definition of the determination time defining unit. The still evaluation unit 73 carries out the walking still state determination based on the still determination time tREF set by the time setting unit 64. The stimulus applying control unit 62 controls the left body stimulus applying unit 90L and the right body stimulus applying unit 90R based on the determination result of the still evaluation unit 73. Thus, an accurate walking still state determination can be carried out according to the walking property of the user 200. An appropriate stimulus applying control thus can be carried out.

Furthermore, the human body stimulus applying device 1 is configured to be able to select the setting method to be used when the measurement unit 72 sets the still determination time tREF. Thus, the still evaluation unit 73 can carry out an accurate walking still state determination according to the walking mode of the user 200. An appropriate stimulus applying control thus can be carried out.

The human body stimulus applying device 1 of the second embodiment has advantages (1) to (6) of the human body stimulus applying device 1 of the first embodiment. In other words, an advantage in that an appropriate stimulus applying control can be carried out, an advantage in that a highly accurate stimulus applying control can be carried out, and other various advantages are obtained by carrying out the walking still state determination in a short period of time while reducing erroneous determinations. The human body stimulus applying device 1 also has the following advantages.

(7) The evaluation unit 70 of the human body stimulus applying device 1 divides the stance phase and the swing phase within one walking cycle into a plurality of movement phases, and carries out the movement determination. The measurement unit 72 measures the movement phase duration time tOP with respect to each of the movement phases divided into plurals. The time setting unit 64 sets the still determination time tREF based on at least one duration time of the duration times of the plurality of divided walking phases measured by the measurement unit 72 before the current walking cycle. The still evaluation unit 73 carries out the walking still state determination based on the still determination time tREF set by the time setting unit 64. The stimulus applying control unit 62 controls the left body stimulus applying unit 90L and the right body stimulus applying unit 90R based on the determination result of the still evaluation unit 73. Thus, an accurate walking still state determination is carried out according to the walking property of the user 200. An appropriate stimulus applying control is thus carried out.

(8) The human body stimulus applying device 1 is configured to select the setting method to be used when the measurement unit 72 sets the still determination time tREF. Thus, the measurement unit 72 measures the duration time of the movement phase with respect to each of the plurality of movement phases. The still evaluation unit 73 carries out an accurate walking still state determination according to the walking mode of the user 200. An appropriate stimulus applying control is thus carried out.

Third Embodiment

The human body stimulus applying device 1 of the third embodiment has a configuration different in the following portions compared to the human body stimulus applying device 1 of the second embodiment, and the same configuration in other portions. The same reference numerals are denoted on the configurations common with the human body stimulus applying device 1 of the second embodiment, and the description thereof will be partially or entirely omitted.

In the human body stimulus applying device 1 of the second embodiment, the first attachment unit 10L includes the left body stimulus applying unit 90L and the second attachment unit 10R includes the right body stimulus applying unit 90R. In the human body stimulus applying device 1 of the third embodiment, on the other hand, the first attachment unit 10L includes a left body electrical stimulus applying portion 140L and the second attachment unit 10R includes a right body electrical stimulus applying portion 140R.

A configuration of the first attachment unit 10L will be described using FIG. 12.

Figure 12:
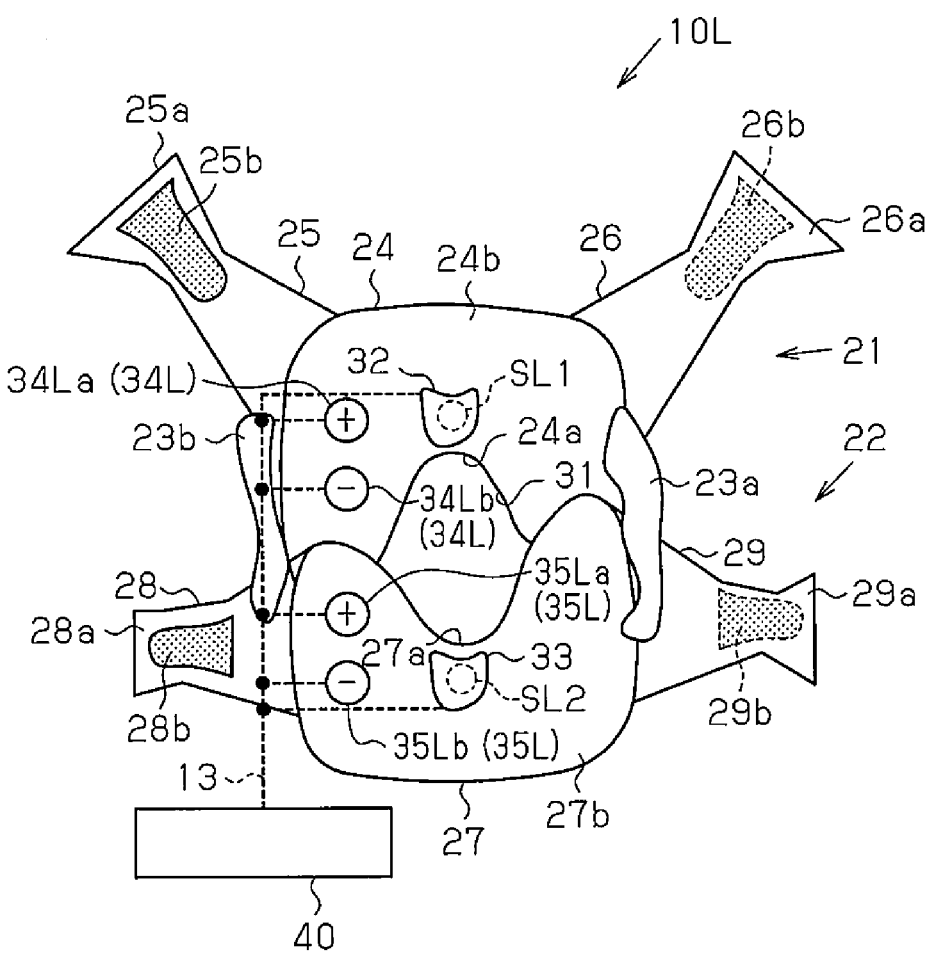
FIG. 12 is a block configuration diagram of the human body stimulus applying device according to a third embodiment of the present invention.

In FIG. 12, the same reference numerals are denoted on the same elements as the first attachment unit 10L in the first embodiment shown in FIG. 3, and the redundant description will be omitted. The second attachment unit 10R has the same configuration as the first attachment unit 10L, and thus the description thereof will be omitted.

The first attachment unit 10L includes the left body electrical stimulus applying portion 140L for applying an electrical stimulus to the body of the user, which left body electrical stimulus applying portion 140L includes an electrode unit 34L arranged on the upper thigh front portion 24, and an electrode unit 35L arranged on the lower thigh front portion 27. The electrode unit 34L includes a pair of positive electrode 34La and negative electrode 34Lb partially exposed from a rear surface 24b of the upper thigh front portion 24. The electrode unit 35L includes a pair of positive electrode 35La and negative electrode 35Lb partially exposed from a rear surface 27b of the lower thigh front portion 27. The exposed portions of the positive electrodes 34La, 35La and the negative electrodes 34Lb, 35Lb are directly brought into contact with the skin to apply the electrical stimulus.

Figure 13:
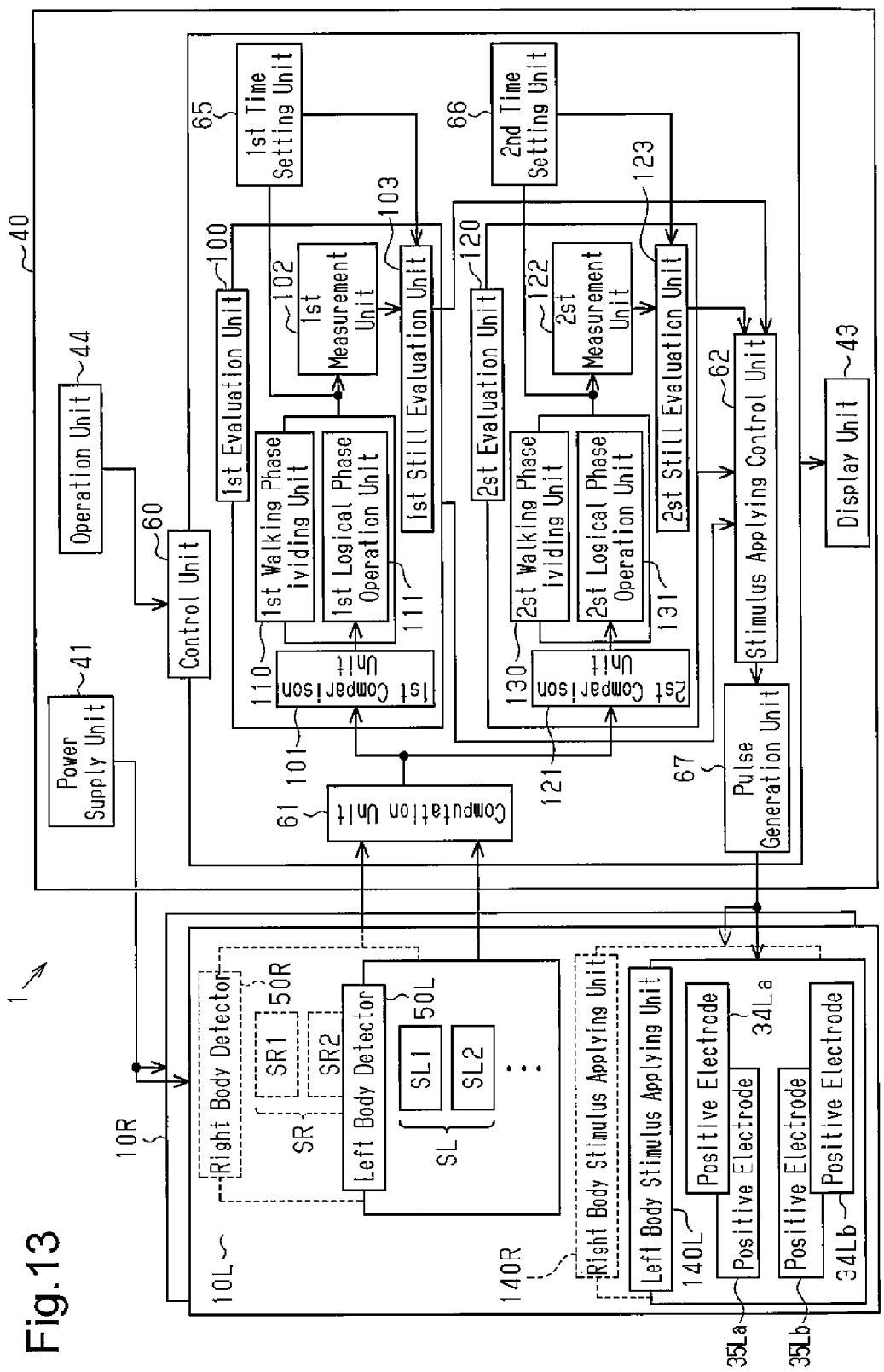
FIG. 13 is a rear view of the attachment unit according to the third embodiment of the present invention.

A circuit block configuration of the human body stimulus applying device 1 will now be described with reference to FIG. 13.

The control unit 60 arranged in the stimulation device main body unit 40 of the human body stimulus applying device 1 includes a first evaluation unit 100, a second evaluation unit 120, a first time setting unit 65, and a second time setting unit 66. The first attachment unit 10L of the human body stimulus applying device 1 includes the left body electrical stimulus applying portion 140L. The second attachment unit 10R of the human body stimulus applying device 1 includes the right body electrical stimulus applying portion 140R.

The first evaluation unit 100 carries out the movement determination of one limb of the user based on the detection result of the left leg detecting unit SL including the first left body sensor SL1 and the second left body sensor SL2 attached to the left body of the user 200 divided by the reference plane 200C. The first evaluation unit 100 includes a first comparison unit 101, a first measurement unit 102, a first still evaluation unit 103, and a first walking phase dividing unit 110. The first walking phase dividing unit 110 includes a first logical operation unit 111. The computation unit 61 carries out the arithmetic processing on the detection signal generated by the left leg detection unit SL. The first comparison unit 101 compares the computation result of the computation unit 61 with a threshold. The first logical operation unit 111 carries out the logical operation on the comparison result provided from the first comparison unit 101. The first evaluation unit 100 uses the first comparison unit 101 and the first logical operation unit 111 to carry out the determination on the first detection signal IL1 of the first left body sensor SL1, the second detection signal IL2 of the second left body sensor SL2, and the like processed by the computation unit 61. Thus, the first evaluation unit 100 determines the plurality of movement phases shown in FIG. 6, that is, the first movement phase OP1, the second movement phase OP2, and the third movement phase OP3 from the walking movement of one walking cycle of the left leg of the user 200. When determining that the movement phase switched with the walking movement, the first evaluation unit 100 provides the movement phase number OPN indicating the first movement phase OP1, the second movement phase OP2, and the third movement phase OP3, and the signal indicating that the movement phase is switched.

The first measurement unit 102 carries out the operations shown in steps S47 to S49 of the walking still determining process shown in FIG. 11 to measure the duration times of the first movement phase OP1, the second movement phase OP2, and the third movement phase OP3 determined by the first evaluation unit 100. The first time setting unit 65 uses the still determination time setting method shown in FIG. 10 to set the still determination time tREF in step S46 of the walking still determining process flowchart shown in FIG. 11. The first still evaluation unit 103 compares the duration times of the first movement phase OP1, the second movement phase OP2, and the third movement phase OP3 measured by the first measurement unit 102 with the still determination time tREF. The first still evaluation unit 103 determines that the walking movement is still if the duration times of the first movement phase OP1, the second movement phase OP2, and the third movement phase OP3 are greater than the still determination time tREF.

The second evaluation unit 120 carries out the movement determination of the other limb of the user based on the detection result of the right leg detecting unit SR including the first right body sensor SR1 and the second right body sensor SR2 attached to the right body of the user 200 divided by the reference plane 200C. The second evaluation unit 120 includes a second comparison unit 121, a second measurement unit 122, a second still evaluation unit 123, and a second walking phase dividing unit 130. The second walking phase dividing unit 130 includes a second logical operation unit 131. The computation unit 61 carries out the arithmetic processing on the detection signal generated by the right leg detection unit SR. The second comparison unit 121 compares the computation result of the computation unit 61 with a threshold. The second logical operation unit 131 carries out the logical operation on the comparison result provided from the second comparison unit 121. The second evaluation unit 120 uses the second comparison unit 121 and the second logical operation unit 131 to carry out the determination on the third detection signal IR1 of the first right body sensor SR1, the fourth detection signal IR2 of the second right body sensor SR2, and the like processed by the computation unit 61. Thus, the second evaluation unit 120 determines the plurality of movement phases shown in FIG. 6, that is, the first movement phase OP1, the second movement phase OP2, and the third movement phase OP3 from the walking movement of one walking cycle of the right leg of the user 200. When determining that the movement phase switched with the walking movement, the second evaluation unit 120 provides the movement phase number OPN indicating the first movement phase OP1, the second movement phase OP2, and the third movement phase OP3, and the signal indicating that the movement phase is switched.

The second measurement unit 122 carries out the operations shown in steps S47 to S49 of the walking still determining process shown in FIG. 11 to measure the duration times of the first movement phase OP1, the second movement phase OP2, and the third movement phase OP3 determined by the second evaluation unit 120. The second time setting unit 66 uses the still determination time setting method shown in FIG. 10 to set the still determination time tREF in step S46 of the walking still determining process flowchart shown in FIG. 11. The second still evaluation unit 123 compares the duration times of the first movement phase OP1, the second movement phase OP2, and the third movement phase OP3 measured by the second measurement unit 122 with the still determination time tREF. The second still evaluation unit 123 determines that the walking movement is still if the duration times of the first movement phase OP1, the second movement phase OP2, and the third movement phase OP3 are greater than the still determination time tREF.

The stimulus applying control unit 62 receives the determination signals from the first still evaluation unit 103 and the second still evaluation unit 123, and controls the left body electrical stimulus applying portion 140L attached to the first attachment unit 10L and the right body electrical stimulus applying portion 140R attached to the second attachment unit 10R based on the determination signals. The stimulus applying control unit 62 receives the determination signals from the first still evaluation unit 103 and the second still evaluation unit 123, and changes the magnitude of the stimulus application on the user 200 based on the determination signals. When the first still evaluation unit 103 determines that the walking movement is still, the left body electrical stimulus applying portion 140L weakens the stimulating power on the user 200 or stops the stimulus application. When the second still evaluation unit 123 determines that the walking movement is still, the right body electrical stimulus applying portion 140R weakens the stimulating power on the user 200 or stops the stimulus application.

The control unit 60 drives a pulse generator 67 based on a control signal from the stimulus applying control unit 62, and generates an electrical stimulating pulse. The left body electrical stimulus applying portion 140L uses the electrical stimulating pulse generated by the pulse generator 67 to generate a predetermined pulse signal between the positive electrode 34La and the negative electrode 34Lb of the electrode unit 34L, and between the positive electrode 35La and the negative electrode 35Lb of the electrode unit 35L. Each of the electrode units 34L and 35L applies the electrical stimulus on the user 200 by the generation of the pulse signal. The right body electrical stimulus applying portion 140R carries out the operation similar to the left body electrical stimulus applying portion 140L, and applies the electrical stimulus on the user 200.

The operation of the electrical stimulating pulse application in the walking movement will now be described using FIG. 14.

In FIG. 14, the movement of the right leg 210R of the user 200 is shown.

FIG. 14A shows the walking movement. Each of the period of time t11 to t21 and the period of time t21 to t31 is one walking cycle period. In the zone of time t21 to t31, the user 200 carries out the walking movement in a walking cycle B shorter than a walking cycle A in the zone of time t11 to t21. The user 200 is in the walking still state after time t31.

FIG. 14B shows the movement phases determined by the first evaluation unit 100. In FIG. 14B, an example in which one walking cycle is divided into four types of movement phases indicated with the first movement phase OP1 to the fourth movement phase OP4 is shown.

FIG. 14C shows a value of the still determination time tREF set for the walking still state determination. As shown in FIG. 14C, the value of the still determination time tREF in the walking cycle B, in which the walking cycle is short, is set to a value smaller than in the walking cycle A.

FIG. 14D shows the movement phase duration time tOP measured by the first measurement unit 102. The value of tOP is set to zero when the movement phase is switched.

FIG. 14E shows a state of the electrical stimulating pulse generated in the pulse generator 67. In the example shown in FIG. 14E, the electrical stimulating pulse is controlled to be turned ON at time t12 and time t23 when the walking movement is switched from the second movement phase OP2 to the third movement phase OP3. The electrical stimulating pulse is controlled to be turned OFF at time t22 when the walking movement is switched from the first movement phase OP1 to the second movement phase OP2. When determined that the walking movement is still, the stimulus applying control unit 62 carries out the control to turn OFF the electrical stimulating pulse.

When the walking movement comes to rest after time t31, the movement phase duration time tOP measured by the first measurement unit 102 increases with time. The second still evaluation unit 123 determines that the walking movement is still at time t32 when the movement phase duration time tOP becomes greater than the still determination time tREF. The stimulus applying control unit 62 carries out the control to turn OFF the electrical stimulating pulse at time t32. The electrical stimulating pulse is maintained in the OFF state during the period in which the walking movement is still after time t32.

The electrical stimulating pulse application with respect to the left leg 210L of the user 200 is carried out at a timing similar to the operation with respect to the right leg 210R according to the movement of the left leg 210L of the user 200 by the human body stimulus applying device 1.

The operation of the human body stimulus applying device 1 will now be described.

The human body stimulus applying device 1 includes the first evaluation unit 100 that determines the movement state of one leg of the user 200. The first evaluation unit 100 includes the first walking phase dividing unit 110, the first measurement unit 102, the first time setting unit 65, and the first still evaluation unit 103. The first evaluation unit 100 determines the movement of one leg of the user 200 based on the detection signal generated by the left leg detection unit SL. The first walking phase dividing unit 110 divides the movement of one leg of the user 200 to a plurality of zones, and determines the movement of the leg in each zone. The first measurement unit 102 measures the movement phase duration time of the movement phase determined with respect to each zone. The first time setting unit 65 sets the still determination time tREF. The first still evaluation unit 103 compares the movement phase duration time with the still determination time tREF, and determines the walking still state.

The human body stimulus applying device 1 includes the second evaluation unit 120 that determines the movement state of the other leg of the user 200. The second evaluation unit 120 includes the second walking phase dividing unit 130, the second measurement unit 122, the second time setting unit 66, and the second still evaluation unit 123. The second evaluation unit 120 determines the movement of the other leg of the user 200 based on the detection signal generated by the right leg detection unit SR. The second walking phase dividing unit 130 divides the movement of the other leg of the user 200 to a plurality of zones, and determines the movement of the leg in each zone. The second measurement unit 122 measures the movement phase duration time of the movement phase determined with respect to each zone. The second time setting unit 66 sets the still determination time tREF. The second still evaluation unit 123 compares the movement phase duration time with the still determination time tREF, and determines the walking still state.

The stimulus applying control unit 62 changes the magnitude of the stimulus application on the user 200 when determined that the walking movement is still based on the determination result of the first still evaluation unit 103. The stimulus applying control unit 62 changes the magnitude of the stimulus application on the user 200 when determined that the walking movement is still based on the determination result of the second still evaluation unit 123. Thus, in the walking movement of the user 200 having a difference in the movements of the left and right legs, the human body stimulus applying device 1 determines the movements of the left and right legs with different evaluation units. Thus, the human body stimulus applying device 1 can carry out the movement phase determination and the walking still state determination with respect to each of the left and right legs. Therefore, an appropriate stimulus applying control can be carried out even with respect to the user carrying out different movements on the left and right.

The first attachment unit 10L of the human body stimulus applying device 1 includes the left body electrical stimulus applying portion 140L, and the second attachment unit 10R of the human body stimulus applying device 1 includes the right body electrical stimulus applying portion 140R. When the first still evaluation unit 103 arranged in the control unit 60 determines that the walking movement is still, the left body electrical stimulus applying portion 140L is controlled to change the magnitude of the stimulus application by the stimulus applying control unit 62. When the second still evaluation unit 123 arranged in the control unit 60 determines that the walking movement is still, the right body electrical stimulus applying portion 140R is controlled to change the magnitude of the stimulus application by the stimulus applying control unit 62. Thus, a zone of applying the electrical stimulus can be set to an appropriate time.

The human body stimulus applying device 1 of the third embodiment has the following advantages in addition to advantages (1) to (6) of the human body stimulus applying device 1 of the first embodiment and advantages (7) and (8) of the human body stimulus applying device 1 of the second embodiment.

(9) The human body stimulus applying device 1 includes the first evaluation unit 100 and the second evaluation unit 120 that determine the movement state of the left and right legs of the user 200, respectively. The first evaluation unit 100 determines the walking still state of one leg of the user 200 based on the movement phase duration time and the still determination time. The second evaluation unit 120 determines the walking still state of the other leg of the user 200 based on the movement phase duration time and the still determination time. The stimulus applying control unit 62 controls the stimulus application to the left and right legs of the user 200 based on the determination results of the first still evaluation unit 103 and the second still evaluation unit 123. According to such configuration, in the walking movement of the user 200 having a difference in the movements of the left and right legs, the human body stimulus applying device 1 determines the movements of the left and right legs with different evaluation units. Thus, the human body stimulus applying device 1 carries out the movement phase determination and the walking still state determination on each left and right legs. Thus, an appropriate stimulus applying control is carried out even with respect to the user carrying out different movements on the left and the right.

(10) The first attachment unit 10L and the second attachment unit 10R of the human body stimulus applying device 1 include the left body electrical stimulus applying portion 140L and the right body electrical stimulus applying portion 140R, respectively. When the first still evaluation unit 103 arranged in the control unit 60 determines that the walking movement is still, the left body electrical stimulus applying portion 140L is controlled to change the magnitude of the stimulus application by the stimulus applying control unit 62. When the second still evaluation unit 123 arranged in the control unit 60 determines that the walking movement is still, the right body electrical stimulus applying portion 140R is controlled to change the magnitude of the stimulus application by the stimulus applying control unit 62. Thus, the human body stimulus applying device 1 sets the zone of applying the electrical stimulus to an appropriate time. The human body stimulus applying device 1 reduces the fatigue caused by the long-time application of the electrical stimulus on the user.

Fourth Embodiment

In the human body stimulus applying device 1 of the fourth embodiment, the set value of the still determination time tREF in one walking cycle is different from the set value in the third embodiment. The stimulus applying control unit 62 provides the control signal to the pulse generator 67 after a predetermined time has elapsed from when the walking still time, which is the elapsed time from when the first still evaluation unit 103 and the second still evaluation unit 123 carry out the walking still determination, exceeded a determination elapsed time. The human body stimulus applying device 1 has the same configuration as the third embodiment, and hence the description on the operation thereof will be omitted.

The operation of the electrical stimulating pulse application in the walking movement will be described using FIG. 15.

FIG. 15A shows the walking movement. Each of the period of time t11 to t21 and the period of time t21 to t31 is one walking cycle period. In the zone of time t21 to t31, the user 200 carries out the walking movement in the walking cycle B shorter than the walking cycle A in the zone of time t11 to t21. The user 200 is in the walking still state after time t31.

FIG. 15B shows the movement phase determined by the first evaluation unit 100. In FIG. 15B, an example in which one walking cycle is divided into four types of movement phases indicated with the first movement phase OP1 to the fourth movement phase OP4 is shown.

FIG. 15C shows a value of the still determination time tREF set for the walking still state determination. As shown in FIG. 15C, different values of the still determination time tREF are set according to the movement phase in the one walking cycle. The still determination time tREF can be changed by changing the proportionality coefficient k with respect to the movement phase duration time tOP shown in FIG. 10 according to the movement phase.

FIG. 15D shows the movement phase duration time tOP measured by the first measurement unit 102. The value of the movement phase duration time tOP is set to zero when the movement phase is switched.

FIG. 15E shows a state of the electrical stimulating pulse generated by the pulse generator 67. In the example shown in FIG. 15E, the electrical stimulating pulse is controlled to be turned ON at time t12 and time 23 when the walking movement is switched from the second movement phase OP2 to the third movement phase OP3. The electrical stimulating pulse is controlled to be turned OFF at time t22 when the walking movement is switched from the first movement phase OP1 to the second movement phase OP2. When determined that the walking movement is still, the stimulus applying control unit 62 carries out the control to turn OFF the electrical stimulating pulse.

When the walking movement comes to rest after time t31, the movement phase duration time tOP measured by the first measurement unit 102 increases with time. The second still evaluation unit 123 determines that the walking movement is still at time t32 when the movement phase duration time tOP becomes greater than the still determination time tREF. The stimulus applying control unit 62 carries out the control to turn OFF the electrical stimulating pulse at time t33, at which a predetermined time has elapsed from time t32. The electrical stimulating pulse is maintained in the OFF state during the walking still state period after time t33.

The human body stimulus applying device 1 of the fourth embodiment has the following advantages in addition to advantages (1) to (6) of the human body stimulus applying device 1 of the first embodiment, advantages (7) and (8) of the human body stimulus applying device 1 of the second embodiment, and advantages (9) and (10) of the human body stimulus applying device 1 of the third embodiment.

(11) The set value of the still determination time tREF set to be used in the walking still state determination is changed according to the movement phase within the one walking cycle. In the walking movement, the walking still state is in the standing position in the majority of the cases. Thus, in the stance phase, the state transitions to the walking still state through the standing state in most cases. The walking still state determination is thus carried out more quickly by setting the set value of the still determination time tREF of the movement phase in the stance phase to a small value. The still determination time becomes longer and erroneous determinations are reduced by setting the set value of the still determination time tREF of the movement phase in the swing phase to a large value. Thus, a highly accurate stimulus applying control is carried out.

(12) The stimulus applying control unit 62 carries out the control of turning OFF the electrical stimulating pulse after elapse of a predetermined time from when the first still evaluation unit 103 and the second still evaluation unit 123 carry out the walking still state determination in the walking movement. Thus, the electrical stimulus application with respect to the user 200 is stopped after the movement of the user 200 shifts from the walking state to the walking still state and a stable walking still state is obtained. Thus, the human body stimulus applying device 1 prevents the user 200 from falling due to the stopping of the stimulus application in the unstable walking still state.

Other Embodiments

Variants of the first to fourth embodiments serving as other embodiments of the human body stimulus applying device will be described below. Each variant below can be combined with each other.

In the human body stimulus applying device 1 of the second to fourth embodiments, the time setting unit 64, the first time setting unit 65, and the second time setting unit 66 divide one walking cycle into a plurality of zones, and sets the still determination time tREF in the respective zones. The configuration of the human body stimulus applying device 1, however, is not limited to the content illustrated in the second to fourth embodiments. For example, in the human body stimulus applying device 1 of the variant, the time setting unit 64, the first time setting unit 65, and the second time setting unit 66 divide one walking cycle into a plurality of zones, and sets the still determination time tREF unified in the plurality of zones.

The operation of the electrical stimulating pulse application in the walking movement will be described using FIG. 16.

The still determination time tREF in each walking cycle is set using the value of the movement phase duration time tOP1 in the first movement phase OP1. In such configuration, the configurations of the time setting unit 64, the first time setting unit 65, and the second time setting unit 66 are simplified.

In the human body stimulus applying device 1 of the third embodiment and the fourth embodiment, the left body electrical stimulus applying portion 140L and the right body electrical stimulus applying portion 140R apply the electrical stimulating pulse on the user 200 upon receiving the signal of the pulse generator 67. However, the configuration of the human body stimulus applying device 1 is not limited to the content illustrated in the second to fourth embodiments. For example, in the human body stimulus applying device 1 according to the variant, the left body electrical stimulus applying portion 140L and the right body electrical stimulus applying portion 140R apply the electrical stimulus to the user 200 by the current that gradually increases with elapse of time. The electrical stimulus may be applied to the user 200 by the current that gradually decreases with elapse of time.

In the human body stimulus applying device 1 of the second embodiment, the determination time defining unit of the time setting unit 64 defines the still determination time tREF with reference to the result of the walking test conducted beforehand on a plurality of subjects. However, the configuration of the human body stimulus applying device 1 is not limited to the content illustrated in the second embodiment. For example, in the human body stimulus applying device 1 of the variant, the determination time defining unit of the time setting unit 64 calculates the still determination time tREF using a calculation formula obtained from the result of the walking test conducted beforehand on the plurality of subjects.

In the human body stimulus applying device 1 of the first to fourth embodiments, the first left body sensor SL1 and the first right body sensor SR1 are angular speed sensors. The second left body sensor SL2 and the second right body sensor SR2 are angular speed sensors. However, the configuration of the human body stimulus applying device 1 is not limited to the contents illustrated in the first to fourth embodiments. For example, in the human body stimulus applying device 1 of the variant, the first left body sensor SL1, the second left body sensor SL2, the first right body sensor SR1, and the second right-side-body sensor SR2 may be the same type of sensor. Alternatively, the first left body sensor SL1, the second left body sensor SL2, the first right body sensor SR1, and the second right body sensor SR2 may be a rotary encoder, a potentiometer, a goniometer, an acceleration sensor, an angular speed sensor, and the like.

In the human body stimulus applying device 1 of the first to fourth embodiments, the first left body sensor SL1, the second left body sensor SL2, the first right body sensor SR1, and the second right body sensor SR2 are connected with the stimulation device main body unit 40 by the connection cable 13. However, the configuration of the human body stimulus applying device 1 is not limited to the contents illustrated in the first to fourth embodiments. For example, in the human body stimulus applying device 1 of the variant, the first left body sensor SL1, the second left body sensor SL2, the first right body sensor SR1, and the second right body sensor SR2, and the stimulation device main body unit 40 may include a wirelessly communicable communication unit.

In the human body stimulus applying device 1 of the first to fourth embodiments, the first left body sensor SL1, the second left body sensor SL2, the first right body sensor SR1, and the second right body sensor SR2 are attached to a knee joint area of the user. However, the configuration of the human body stimulus applying device 1 is not limited to the contents illustrated in the first to fourth embodiments. For example, in the human body stimulus applying device 1 of the variant, the first left body sensor SL1, the second left body sensor SL2, the first right body sensor SR1, and the second right body sensor SR2 may be attached around the hip joint of the user. Alternatively, the first left body sensor SL1, the second left body sensor SL2, the first right body sensor SR1, and the second right body sensor SR2 may be attached to other regions such as the hip, elbow, arm, ankle, and the like of the user. In this case, the first left body sensor SL1, the second left body sensor SL2, the first right body sensor SR1, and the second right body sensor SR2 are attached to regions symmetrical with respect to the reference plane. The first left body sensor SL1, the second left body sensor SL2, the first right body sensor SR1, and the second right body sensor SR2 are preferably arranged at positions sandwiching the joint of the body of the user in between.

In the human body stimulus applying device 1 of the first to fourth embodiments, the first attachment unit 10L and the second attachment unit 10R are configured as separate bodies from the stimulation device main body unit 40. However, the configuration of the human body stimulus applying device 1 is not limited to the contents illustrated in the first to fourth embodiments. For example, in the human body stimulus applying device 1 of the variant, the stimulation device main body unit 40 may be incorporated in the first attachment unit 10L and the second attachment unit 10R.

In the human body stimulus applying device 1 of the third embodiment, the first evaluation unit 100 carries out the movement determination of one leg, and the second evaluation unit 120 carries out the movement determination of the other leg. Similarly, the movement determination of the other leg is also carried out based on the determination results of the first evaluation unit 100 and the second evaluation unit 120. However, the configuration of the human body stimulus applying device 1 is not limited to the content illustrated in the third embodiment. For example, in the human body stimulus applying device 1 of the variant, the first evaluation unit 100 and the second evaluation unit 120 may carry out the movement determination of one leg, and the first evaluation unit 100 and the second evaluation unit 120 may carry out the movement determination of the other leg.

In the human body stimulus applying device 1 of the first to fourth embodiments, the left leg detection unit SL includes the first left body sensor SL1 and the first right body sensor SR1 of the same type. The right leg detection unit SR includes the second left body sensor SL2 and the second right body sensor SR2 of the same type. However, the configuration of the human body stimulus applying device 1 is not limited to the contents illustrated in the first to fourth embodiments. For example, in the human body stimulus applying device 1 of the variant, the left leg detection unit SL and the right leg detection unit SR may each include a different type of sensor. Accordingly, the first evaluation unit 100 and the second evaluation unit 120 carry out the movement determination of the user 200 using the detection values of the different sensors.

In the human body stimulus applying device 1 of the third embodiment, the stimulus applying control unit 62 controls the pulse generator 67 to generate the electrical stimulating pulse. However, the configuration of the human body stimulus applying device 1 is not limited to the content illustrated in the third embodiment. For example, in the human body stimulus applying device 1 of the variant, the electrical stimulus is applied by the current that gradually increases with elapse of time.

In the human body stimulus applying device 1 of the first to fourth embodiments, the left leg detection unit SL is arranged in the left body detector 50L, and the right leg detection unit SR is arranged in the right body detector 50R. However, the configuration of the human body stimulus applying device 1 is not limited to the contents illustrated in the first to fourth embodiments. For example, in the human body stimulus applying device 1 of the variant, the detection unit includes an auxiliary detection unit including at least one sensor to be attached to a human body. Accordingly, even if the left leg detection unit SL and the right leg detection unit SR both make erroneous detections, the auxiliary detection unit detects the movement of the human body in place of the left leg detection unit SL and the right leg detection unit SR. Thus, the movement detection of the human body is carried out on the basis of higher reliability.

The human body stimulus applying device 1 of the first to fourth embodiments divides the walking movement of the user 200 into a plurality of zones, and carries out the movement determination with respect to each zone. However, the configuration of the human body stimulus applying device 1 is not limited to the contents illustrated in the first to fourth embodiments. For example, the human body stimulus applying device 1 of the variant may carry out the movement determination in the up/down movement of the stairs, and the like, and may apply stimulus. Alternatively, the human body stimulus applying device 1 may carry out the movement determination in the rising movement from the legless chair, and the like, and may apply stimulus.

The first to fourth embodiments configure the human body stimulus applying device 1 serving as an application example of the body motion detection device. However, the application of the body motion detection device is not limited to the human body stimulus applying device. For example, the body motion detection device of the variant may be applied to a fall preventing device in medical services. The fall preventing device determines the walking state of the physically impaired patient, and accumulates the determination data. The fall preventing device determines the walking state of when the patient is walking, and predicts the fall based on the accumulated determination data.

The fall preventing device divides the walking state into a plurality of movement phases and accumulates the detailed movement determination data including the still determination to make a highly accurate prediction.

The invention claimed is:

1. A body motion detection device that detects movement of a human body, the body motion detection device comprising:
   a detection unit that generates a detection signal that changes according to a walking movement of the human body; and
   an evaluation unit that separates the walking movement of one walking cycle into a plurality of walking phases based on the detection signal generated by the detection unit, wherein the evaluation unit determines whether or not the walking movement is still based on a duration time of at least one of the walking phases, wherein:
   the one walking cycle includes a stance phase and a swing phase that defined as specific walking phases; and
   the evaluation unit determines divided walking phases within the stance phase or the swing phase based on the detection signal, and determines whether or not the walking movement is still based on a duration time of at least one of the divided walking phases.

2. The body motion detection device according to claim 1, wherein the evaluation unit determines that the walking movement is still when the duration time of at least one of the divided walking phases is longer than a still determination time.

3. The body motion detection device according to claim 2, wherein
   the evaluation unit includes a measurement unit that measures the duration time of each of the divided walking phases; and
   the evaluation unit determines whether or not the walking movement is still based on a comparison of the duration time of at least one of the divided walking phases measured by the measurement unit with the still determination time.

4. The body motion detection device according to claim 3, further comprising a time setting unit that sets the still determination time based on the duration time of at least one of the walking phases measured by the measurement unit.

5. The body motion detection device according to claim 4, wherein the time setting unit sets the still determination time based on at least one of the duration times measured by the measurement unit before a current walking cycle.

6. The body motion detection device according to claim 4, wherein the time setting unit includes a determination time defining unit that sets a relationship of the duration time of each of the divided walking phases and the still determination time, wherein the determination time defining unit outputs the still determination time based on the relationship when the duration time of the divided walking phase is received from the measurement unit.

7. The body motion detection device according to claim 1, wherein
   the detection unit includes
   a right body detector including a first right body sensor that generates an output signal corresponding to a movement of a first right body region and a second right body sensor that generates an output signal corresponding to a movement of a second right body region, and
   a left body detector including a first left body sensor that generates an output signal corresponding to a movement of a first left body region and a second left body sensor that generates an output signal corresponding to a movement of a second left body region; and
   the evaluation unit determines whether or not the walking movement is still based on at least one of the output signal of the first right body sensor, the output signal of the first left body sensor, the output signal of the second right body sensor, and the output signal of the second left body sensor.

8. A human body stimulus applying device that applies stimulus to a human body, the human body stimulus applying device comprising:
   the body motion detection device according to claim 1;
   a control unit that transmits a command signal to a stimulus applying portion based on a determination result of the body motion detection device; and
   a stimulus applying portion that changes a magnitude of the stimulus to apply to the human body based on the command signal.

9. The human body stimulus applying device according to claim 8, wherein
   the stimulus applying portion includes a right body stimulus applying portion that applies stimulus to a right body, and a left body stimulus applying portion that applies stimulus to a left body;
   the evaluation unit includes,
   a first evaluation unit that determines whether or not the walking movement is still based on the output signal of the first right body sensor and the output signal of the second right body sensor, and a second evaluation unit that determines whether or not the walking movement is still based on the output signal of the first left body sensor and the output signal of the second left body sensor; and the control unit transmits a command signal to the right body stimulus applying portion and applies stimulus to the human body when the first evaluation unit determines that the walking movement is still, and the control unit transmits a command signal to the left body stimulus applying portion to have stimulus applied to the human body when the second evaluation unit determines that the walking movement is still.

10. The human body stimulus applying device according to claim 8, wherein the control unit transmits the command signal to the stimulus applying portion after a walking still time, which is an elapsed time from when determined that the walking movement is still, exceeds a determination elapsed time.

11. The human body stimulus applying device according to claim 8, wherein the stimulus applying portion applies an electrical stimulus to the human body.

\* \* \* \* \*